US011517348B2

(12) United States Patent
Abboud

(10) Patent No.: US 11,517,348 B2
(45) Date of Patent: Dec. 6, 2022

(54) GUIDE DEVICE SUITABLE FOR PERFORMING TEMPOROMANDIBULAR JOINT ARTHROSCOPY

(71) Applicant: TEL HASHOMER MEDICAL RESEARCH INFRASTRUCTURE AND SERVICES LTD., Ramat Gan (IL)

(72) Inventor: Waseem Abboud, Ramat Gan (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 399 days.

(21) Appl. No.: 16/609,492

(22) PCT Filed: May 3, 2018

(86) PCT No.: PCT/IL2018/050488
§ 371 (c)(1),
(2) Date: Oct. 30, 2019

(87) PCT Pub. No.: WO2018/203338
PCT Pub. Date: Nov. 8, 2018

(65) Prior Publication Data

US 2020/0060724 A1 Feb. 27, 2020

Related U.S. Application Data

(60) Provisional application No. 62/500,517, filed on May 3, 2017.

(51) Int. Cl.
*A61B 17/34* (2006.01)
*A61B 90/57* (2016.01)
(Continued)

(52) U.S. Cl.
CPC ...... *A61B 17/3423* (2013.01); *A61B 17/3403* (2013.01); *A61B 90/57* (2016.02);
(Continued)

(58) Field of Classification Search
CPC . A61B 17/34; A61B 17/3423; A61B 17/3403; A61B 90/50; A61B 90/57
See application file for complete search history.

(56) References Cited

U.S. PATENT DOCUMENTS 4,672,957 A 6/1987 Hourahane
4,708,139 A 11/1987 Dunbar, IV
(Continued)

FOREIGN PATENT DOCUMENTS

DE 3339259 3/1985
DE 102013222005 A1 4/2015
(Continued)

OTHER PUBLICATIONS

International Search Report, International Application No. PCT/IL2018/050488, dated Aug. 15, 2018.
(Continued)

*Primary Examiner* — Christopher J Beccia
(74) *Attorney, Agent, or Firm* — The Roy Gross Law Firm, LLC; Roy Gross

(57) ABSTRACT

A guide device for TMJ arthroscopy including one or more pairs of arms pivotly connected at one end to a working cannula holder and defining a working cannula axis; and at the opposite end to at one or more arms via one or more pivot connections to form with the arm one or more adjustable parallelograms, an end of the arm is connected to an irrigation cannula holder defining an irrigation cannula axis, the irrigation cannula axis intersecting with the working cannula axis at an intersection, intersection and one or more of the pivot connections between connecting the arms are
(Continued)

located at opposing vertices of one or more of the adjustable parallelograms.

13 Claims, 11 Drawing Sheets

(51) Int. Cl.

| | |
|---|---|
| *A61B 90/50* | (2016.01) |
| *A61B 1/317* | (2006.01) |
| *A61B 17/00* | (2006.01) |

(52) U.S. Cl.

CPC ..... *A61B 1/317* (2013.01); *A61B 2017/00424* (2013.01); *A61B 2017/3407* (2013.01); *A61B 2090/506* (2016.02)

(56) References Cited

U.S. PATENT DOCUMENTS

| | | | | |
|---|---|---|---|---|
| 4,769,018 | A | 9/1988 | Wilson | |
| 4,781,182 | A | 11/1988 | Purnell et al. | |
| 4,920,958 | A | 5/1990 | Walt et al. | |
| 5,397,323 | A * | 3/1995 | Taylor | A61B 34/71 901/41 |
| 5,797,835 | A * | 8/1998 | Green | A61B 1/00147 600/113 |
| 5,824,007 | A * | 10/1998 | Faraz | F16M 11/046 600/102 |
| 6,246,200 | B1 * | 6/2001 | Blumenkranz | A61B 34/70 318/568.25 |
| 7,717,919 | B2 | 5/2010 | Assell et al. | |
| 2003/0109825 | A1 * | 6/2003 | Loser | A61B 17/3403 604/131 |
| 2012/0316575 | A1 | 12/2012 | Farin et al. | |

FOREIGN PATENT DOCUMENTS

| | | | |
|---|---|---|---|
| WO | 1998010822 | A1 | 3/1998 |
| WO | 2007056379 | A2 | 5/2007 |

OTHER PUBLICATIONS

International Preliminary Report on Patentability, International Application No. PCT/IL2018/050488, dated Nov. 5, 2019.

* cited by examiner

GUIDE DEVICE SUITABLE FOR PERFORMING TEMPOROMANDIBULAR JOINT ARTHROSCOPY

CROSS-REFERENCE TO RELATED APPLICATIONS

This application is a National Phase of PCT Patent Application No. PCT/IL2018/050488 having International filing date of May 3, 2018, which claims the benefit of priority of U.S. Provisional Patent Application No. 62/500,517, filed on May 3, 2017. The contents of the above applications are all incorporated by reference as if fully set forth herein in their entirety.

FIELD AND BACKGROUND OF THE INVENTION

The invention, in some embodiments, relates to the field of surgical guides, and more specifically, to a guide device suitable for assisting in performing a TMJ arthroscopy procedure.

TMJ arthroscopy is a minimally-invasive surgical procedure that is performed on the TMJ (Temporo-Mandibular Joint, the jaw joint).

In a first step, a surgeon pushes a first cannula (typically with the help of a trocar) through the skin and other tissue to enter the TMJ to define an irrigation aperture channel. Once the distal tip of the first cannula is properly positioned, an irrigation device is inserted into the TMJ through the first cannula and used to force fluid such as saline into the TMJ to cause hydrodistension of the TMJ, forming a relatively large fluid-filled space. The volume of the fluid-filled space is initially about 1 ml, but typically increases during a TMJ arthroscopy procedure to between 5 ml and 8 ml.

A second cannula (typically with the help of a trocar) is pushed through the skin and other tissue to enter the fluid-filled space in the TMJ at an angle (e.g., perpendicularly) to the first cannula to define a working channel as well as to provide a route through which the hydrodistension fluid escapes.

While fluid is continuously forced through the irrigation channel to maintain the fluid-filled space and clear debris and the like released into the fluid-filled space, tools are inserted through the working channel into the fluid-filled space to perform medical procedures as determined by a performing surgeon. The use of the tools inserted through the working channel is directed with the help of an observation device (e.g. an endoscope) that is inserted through the irrigation channel.

Depending on the preference of the surgeon, in some embodiments a cannula is inserted through an aperture to establish a passageway (e.g., the working aperture) that constitutes an irrigation or working channel. In some embodiments, the channels have a similar or identical internal diameter channel. In some embodiments the working channel has a substantially smaller diameter than that of the irrigation channel. The use of similar- or identical-sized cannulae allows a surgeon to switch between channels, inserting an observation device into the TMJ through what was, originally the working channel, and inserting a surgical tool into the TMJ through the irrigation channel.

When the second cannula is inserted into the fluid-filled space at an angle (e.g., perpendicularly) to the first cannula it is challenging (and when not inserted perpendicularly, even more challenging) to insert the second cannula properly into the fluid-filled space where the axis of the second cannula intersects the axis of the first cannula inside the fluid filled space so that an observation device inserted through the irrigation channel can be effectively used to view at least a tip of a tool inserted via the working channel and parts of the TMJ to be treated and so that the tool inserted through the working channel can reach all parts of the TMJ accessible in the fluid-filled space and remain within a field of view (FOV) of the observation device.

If the second cannula is improperly inserted so that it becomes difficult or impossible to direct a tool using the observation device, it typically becomes necessary to remove and reinsert the second cannula, leading to greater trauma and side effects to the treated subject, as well as excess leakage of the fluid pumped into the fluid-filled space. In some instances, two succeeding failures to properly insert the second cannula lead to suspension of the TMJ arthroscopy.

An additional challenge is maintaining the relative orientation of the tips of the two channels in three dimensions so that the observation device can have continuous and uninterrupted line of sight to the tip of the tool used for treating the joint. In the operating theater, much effort is made to ensure the relative orientation of the cannulae: often, the surgeon holds both cannulae and the observation device steady, while the assistant surgeon is tasked with inserting and manipulating the tool itself.

SUMMARY OF THE INVENTION

Some embodiments of the invention relate to a guide device suitable for assisting in performing a TMJ arthroscopy procedure. In some embodiments, the guide device allows accurate insertion and positioning of a cannula (e.g., that constitutes the working channel) relative to a first cannula (that constitutes an irrigation channel). Some embodiments of the guide device of the invention are configured to position one channel (e.g., the working channel) at an angle different from perpendicular to the second channel (e.g., irrigation channel) if desired. For example, to access the TMJ from a direction that is surgically preferred but would not be ordinarily attempted due to, for example, a challenging insertion angle required for insertion of the second cannula. In some embodiments, the guide device is configured to fix a desired relative spatial orientation of the two channels in 3D space, allowing a surgeon to position both channels (and cannulae inserted within) with one hand and use a required tool with the other hand.

For brevity and clarity, in the description of the teachings herein as well as the claims, the term "working channel" is used to refer to a cannula suitable for use as a working channel as known in the art of surgery and the term "irrigation channel" is used to refer to a cannula suitable for use as an irrigation fluid throughway. Suitable cannulae, including cannulae marketed specifically for use in TMJ arthroscopy are readily available from commercial sources (e.g., Karl Storz GmbH&Co, Tuttlingen, Germany; Stryker Corporation, Kalamazoo, Mich., USA; Smith & Nephew, London and Hull, United Kingdom; Olympus Corporation, Shinjuku, Tokyo, Japan).

As used herein, the terms "working channel" and "irrigation channel" are used to differentiate between the two channels. As used in arthroscopy, the channel that is deployed first is initially used for irrigation and observation while the channel that is deployed second is initially used for insertion of tools. The two terms as used herein are not limiting: once both channels are deployed, and the channels may potentially be used interchangeably (e.g., mid-operation). E.g., an irrigation device may be inserted through either the working channel or the irrigation channel and a tool may be inserted through either the working channel or the irrigation channel. Alternatively, and optionally, an observation device may be inserted through either the working channel or the irrigation channel.

According to an aspect of some embodiments of the invention there is provided a guide device useful for assisting in performance of TMJ arthroscopy, including:

a working channel holder defining a working channel axis and an irrigation channel holder defining an irrigation channel axis, the working channel axis and the irrigation channel axis substantially intersecting at an intersection that is within a specific empty volume, at an intersection angle, a plurality of linkages mutually connected by a plurality of parallel-axis revolute joints, the revolute joints defining the vertices of a plurality of parallelograms having sides with fixed lengths with angles changeable by rotation of the linkages around the revolute joints, wherein a first of the plurality of parallelograms includes as vertices two of the revolute joints that are connected to the working channel holder, wherein a second of the plurality of parallelograms includes as vertices two of the revolute joints that are connected to the channel holder, and wherein a third of the plurality of parallelograms includes the intersection (44) as a vertex, and wherein the parallelograms are physically linked so that the distance of the intersection from the working channel holder and from the irrigation channel holder remains constant while the intersection angle changes during the rotation of the linkages around the revolute joints.

The working channel holder is a component configured to hold a cannula suitable for use as a working channel for TMJ arthroscopy coaxially with the working channel axis so as to function as a working channel. Hence, as used herein, the terms "Irrigation Channel axis" and "Irrigation Cannula axis" are used interchangeably herein and refer to the same axis.

Accordingly, and as used herein, the terms "Working Channel axis" and "Working Cannula axis" are used interchangeably herein and refer to the same axis. In some embodiments, a diameter of at least one of the cannulae is between 1 mm and 4 mm. In some embodiments, a diameter of at least one of the cannulae is between 1.5 mm and 3.7 mm. In some embodiments, a diameter of at least one of the cannulae is between 2 mm and 3 mm. The irrigation channel holder is a component configured to hold a cannula suitable for use as an irrigation channel for TMJ arthroscopy coaxially with the irrigation channel axis so as to function as an irrigation channel. In some embodiments, the plurality of linkages includes at least six rigid linkages mutually connected by the plurality of parallel-axis revolute joints which includes at least seven parallel-axis revolute joints, a rigid upper working channel link connected to the working channel holder with a third revolute joint, a rigid lower working channel link connected to the working channel holder with a sixth revolute joint, a rigid proximal transmission link connected to the irrigation channel holder with a seventh revolute joint, a rigid distal transmission link connected to the irrigation channel holder with an eighth revolute joint, and at least three members selected from the group consisting of:

the upper working channel link connected to the proximal transmission link with a first revolute joint, the upper working channel link connected to the distal transmission link with a second revolute joint, the lower working channel link connected to the proximal transmission link with a fourth revolute joint, and the lower working channel link connected to rigid distal transmission link with a fifth revolute joint.

In some embodiments, the first parallelogram has as vertices the second revolute joint, the third revolute joint, the fifth revolute joint, and the sixth revolute joint and as sides the upper working channel link, the lower working channel link, the distal transmission link and the working channel holder, the second parallelogram has as vertices the fourth revolute joint, the fifth revolute joint, the seventh revolute joint, and the eighth revolute joint, and as sides the lower working channel link, the irrigation channel holder, the proximal transmission link and the distal transmission link, and the third parallelogram has as vertices the fifth revolute joint, the sixth revolute joint, the eighth revolute joint, and the intersection, and as sides the lower working channel link, the irrigation channel axis, the distal transmission link and the working channel axis.

In some embodiments, the first parallelogram has as vertices the first revolute joint, the third revolute joint, the fourth revolute joint, and the sixth revolute joint and as sides the upper working channel link, the lower working channel link, the proximal transmission link and the working channel holder, the second parallelogram has as vertices the fourth revolute joint, the fifth revolute joint, the seventh revolute joint, and the eighth revolute joint, and as sides the lower working channel link, the irrigation channel holder, the proximal transmission link and the distal transmission link, and the third parallelogram has as vertices the fourth revolute joint, the sixth revolute joint, the seventh revolute joint, and the intersection, and as sides the lower working channel link, the irrigation channel axis, the proximal transmission link and the working channel axis.

In some embodiments, the first parallelogram has as vertices the second revolute joint, the third revolute joint, the fifth revolute joint, and the sixth revolute joint and as sides the upper working channel link, the lower working channel link, the distal transmission link and the working channel holder, the second parallelogram has as vertices the first revolute joint, the second revolute joint, the seventh revolute joint, and the eighth revolute joint, and as sides the upper working channel link, the irrigation channel holder, the proximal transmission link and the distal transmission link, and the third parallelogram has as vertices the second revolute joint, the third revolute joint, the eighth revolute joint, and the intersection, and as sides the upper working channel link, the irrigation channel axis, the distal transmission link and the working channel axis.

In some embodiments, the first parallelogram has as vertices the first revolute joint, the third revolute joint, the fourth revolute joint, and the sixth revolute joint and as sides the upper working channel link, the lower working channel link, the proximal transmission link and the working channel holder, the second parallelogram has as vertices the first revolute joint, the second revolute joint, the seventh revolute joint, and the eighth revolute joint, and as sides the upper working channel link, the irrigation channel holder, the proximal transmission link and the distal transmission link, and the third parallelogram has as vertices the first revolute joint, the third revolute joint, the seventh revolute joint, and the intersection, and as sides the upper working channel link, the irrigation channel axis, the proximal transmission link and the working channel axis.

In some embodiments, the length of the proximal transmission link and a length of the distal proximal length are adjustable. In some embodiments, the irrigation channel holder is configured to allow rotation around the working channel axis of a working channel held therein.

In some embodiments, all the listed revolute joints are coplanar. In some embodiments, at least a portion of the listed revolute joints are coplanar. In some embodiments, the axes of rotation of the revolute joints are substantially perpendicular to a plane that includes the irrigation channel axis. In some embodiments, the axes of rotation of the revolute joints are substantially perpendicular to a plane that includes the working channel axis.

In some embodiments, the axes of rotation of the revolute joints are perpendicular to a plane that includes both the working channel axis and the irrigation channel axis.

In some embodiments, the axes of rotation of the revolute joints are not perpendicular to a plane that includes both the working channel axis and the irrigation channel axis. In some embodiments, the device further includes a rotation lock, allowing reversible fixing of an angle of rotation of the revolute joints. In some embodiments, the device further includes a working channel lock configured to reversibly secure a working channel held in the working channel holder. In some embodiments, the device further includes an irrigation channel lock configured to reversibly secure an irrigation channel held in the irrigation channel holder. In some embodiments, the working channel holder directly rigidly connects the third and sixth revolute joints.

In some embodiments, the working channel holder includes two physically separate working channel holder parts, a first part connected to the third revolute joint and a second part connected to the sixth revolute joint. In some embodiments, the irrigation channel holder directly rigidly connects the seventh and eighth revolute joints one to the other. In some embodiments, the irrigation channel holder includes two physically separate irrigation channel holder parts, a first part connected to the seventh revolute joint and a second irrigation channel holder part connected to the eighth revolute joint. In some embodiments, the irrigation channel holder is configured to allow reversible physical association of an irrigation channel with the irrigation channel holder.

In some embodiments, the device further includes an irrigation channel physically associated with the irrigation channel holder. In some embodiments, the irrigation channel is reversibly physically associated with the irrigation channel holder. In some embodiments, the irrigation channel holder is a component of the cannula. According to an aspect of some embodiments of the invention, there is provided a system useful for assisting in performance of TMJ arthroscopy, including:

a guide device having a working channel holder defining a working channel axis and an irrigation channel holder defining an irrigation channel axis, the working channel axis and the irrigation channel axis substantially intersecting at an intersection that is within a specific empty volume, at an intersection angle, a plurality of linkages mutually connected by a plurality of parallel-axis revolute joints, the revolute joints defining the vertices of a plurality of parallelograms having sides with fixed lengths with angles changeable by rotation of the linkages around the revolute joints, wherein a first of the plurality of parallelograms includes as vertices two of the revolute joints that are connected to the working channel holder, wherein a second of the plurality of parallelograms includes as vertices two of the revolute joints that are connected to the channel holder, and wherein a third of the plurality of parallelograms includes the intersection (44) as a vertex, and wherein the parallelograms are physically linked so that the distance of the intersection from the working channel holder and from the irrigation channel holder remains constant while the intersection angle changes during the rotation of the linkages around the revolute joints;

a working cannula accommodated within said working channel holder; and an irrigation/viewing cannula accommodated within said irrigation channel holder.

In some embodiments, the system comprises a patch comprising at least one adhesive surface and at least one high-friction coefficient surface. In some embodiments, the patch is configured to adhere to a surface of at least one cannula. In some embodiments, the patch is configured to adhere to a surface of at least one working and irrigation channel. In some embodiments, the patch is resilient and configured to cushion contact between the cannula and the internal surface of the working and/or irrigation channel.

According to an aspect of some embodiments of the invention, there is also provided a kit including: a guide device and a working channel, configured for physical association with the working channel holder of the guide device. In some embodiments, the kit further includes an irrigation channel, configured for physical association with the irrigation channel holder of the guide device.

According to an aspect of some embodiments of the invention, there is also provided a kit including a guide device and an irrigation channel configured for physical association with the irrigation channel holder of the guide device. In some embodiments, the kit further includes a working channel, configured for physical association with the working channel holder of the guide device.

According to an aspect of some embodiments of the invention, there is provided a guide device for TMJ arthroscopy, including at least one pair of arms pivotly connected at one end to a working cannula holder defining a working cannula axis and at the opposite end to at least one arm via at least one pivot connection to form with the arm one or more adjustable parallelograms, an end of the arm connected to an irrigation cannula holder defining an irrigation cannula axis the irrigation cannula axis intersecting with the working cannula axis at an intersection and the intersection and at least one of the pivot connections connecting the arms are located at opposing vertices of at least one of the adjustable parallelograms.

According to some embodiments of the invention, the device includes at least two pairs of arms pivotly connected by parallel-axis revolute joints to form at least one adjustable parallelogram. In some embodiments, at least the pair of arms is connected to the working cannula holder via at least one parallel-axis revolute joint. In some embodiments, the guide device includes at least one locking joint adjustable from an open-unlocked position that allows adjustment of the device arms to a closed-locked position that fixes the orientation of the arms in respect to each other. In some embodiments, the locking joint and the intersection are located at opposing vertices of a largest parallelogram. In some embodiments, the locking joint is controlled by an ergonomic handle.

According to some embodiments of the invention, the guide device includes an ergonomic handle wherein the handle and the intersection are located at opposing vertices of a largest parallelogram. In some embodiments, the channel holder includes a body having a furrow and a cover, at least a surface of the furrow and an inner surface of the cover include at least one layer of a resilient and/or retentive material. In some embodiments, the material includes at least one layer of a high-friction coefficient material and at last one layer of resilient material between the high-friction coefficient material and at least one of the surfaces. In some embodiments, the body holder is configured to concurrently allow movement of a tip of a tool held between the furrow and the cover and retain the tool within the holder. In some embodiments, at least one of the cannula and channel holder includes a cannula insertion limiter.

According to some embodiments, the guide device includes at least one protractor coupled at one end to at least one of the arms and is slidable over at least one adjacent pivotly connected arm. In some embodiments, the protractor is slotted and the adjacent pivotly connected arm includes a pin biased radially outwards in respect to the slot. In some embodiments, the slot includes at least one notch indicating at least one of an angle ($\alpha_{max}$) and an angle ($\alpha_{mx}$). In some embodiments, the guide device is adjustable from a fully extended state to a fully retracted state wherein at the fully extended state the device defines an angle ($\alpha$) between adjacent pivotly connected arms, the angle ($\alpha$) being between 90 and 180 degrees and at the fully retracted state the device defines an angle ($\alpha$) between adjacent pivotly connected arms, the angle ($\alpha$) being between Zero (0) and 20 degrees.

Unless otherwise defined, all technical and scientific terms used herein have the same meaning as commonly understood by one of ordinary skill in the art to which the invention pertains. In case of conflict, the specification, including definitions, will take precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +1-10%.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale. In the Figures:

FIG. 1A in side view in a configuration where the working channel axis is perpendicular to the irrigation channel axis;

FIG. 1B in view from the back;

FIG. 1C in side view with a physically associated irrigation channel where the working part axis is perpendicular to the irrigation channel axis;

FIG. 1D in side view with a physically associated irrigation channel where the working part axis is not perpendicular to the irrigation channel axis;

FIG. 3A in side view;

FIG. 3B in view from the back; and

DESCRIPTION OF SOME EMBODIMENTS OF THE INVENTION

Some embodiments of the invention relate to the field of surgical guides, and more specifically, to a guide device suitable for assisting in performing a TMJ arthroscopy procedure.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As discussed in the background section above, in TMJ arthroscopy, it is challenging to insert and bring at least a tip of the second cannula that constitutes the working channel to the proper location relative to and within the FOV of an observation tool inserted via the first cannula that constitutes the irrigation channel. In some embodiments, a diameter of at least one of the cannulae is between 1 mm and 4 mm. In some embodiments, a diameter of at least one of the cannulae is between 1.5 mm and 3.7 mm. In some embodiments, a diameter of at least one of the cannulae is between 2 mm and 3 mm.

Some embodiments of the invention relate to a guide device suitable for assisting in performing a TMJ arthroscopy procedure that allows accurate insertion of the second cannula (that constitutes a working channel) at an angle and depth relative to the first cannula (that constitutes an irrigation channel) into the TMJ so that at least a tip of a tool inserted via the working channel is viewed within a FOV of an observation tool inserted via the irrigation channel throughout the procedure. Further, some embodiments of the guide device allow a user to choose to insert the working channel at an angle different from perpendicular to the irrigation channel if desired, for example, as decided by the operating surgeon.

First Embodiment of the Device

A first exemplary embodiment of a guide device according to the teachings herein, device 10, is schematically depicted in FIGS. 1A to 1D.

To avoid clutter of the figures that will reduce clarity, not all components are labeled in all of the figures.

Figure 1B:
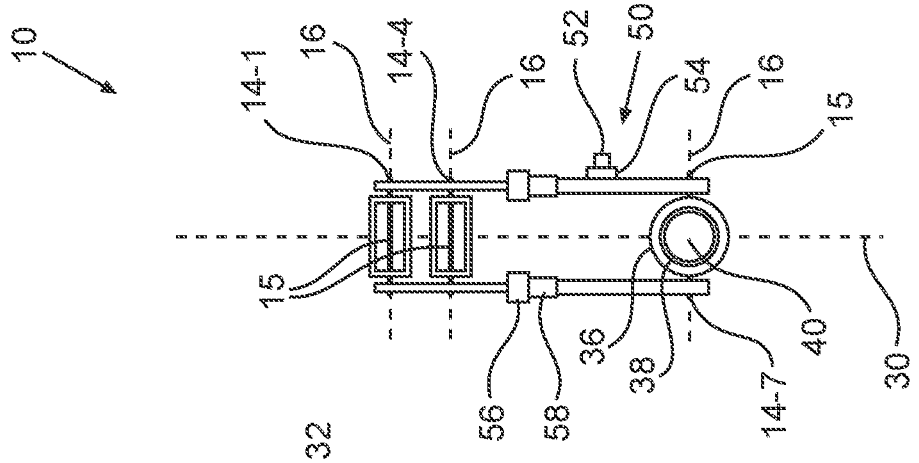
FIGS. 1A to 1D schematically depict a first exemplary embodiment of a guide device according to the teachings herein.
Figure 1A:
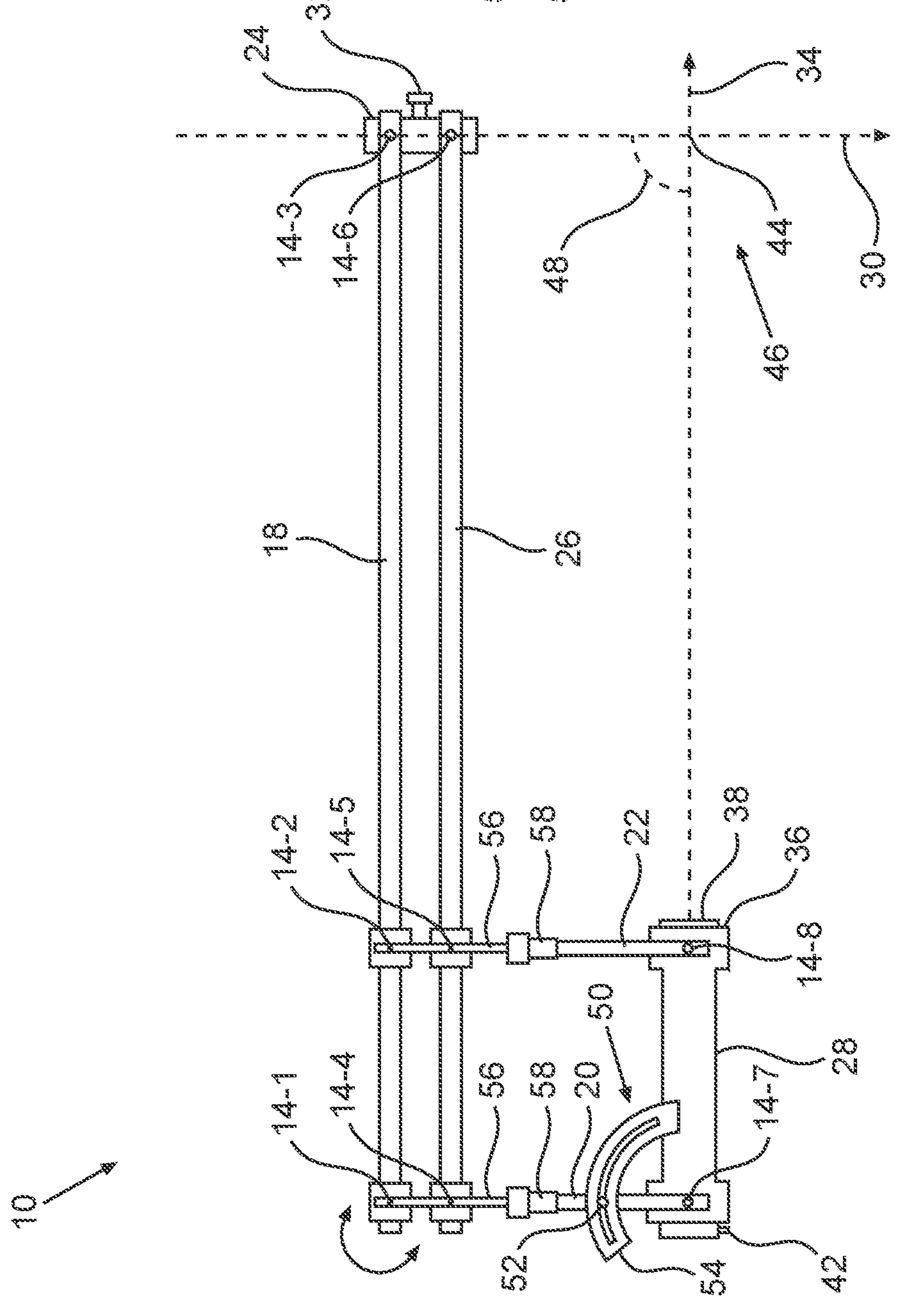
Figure 1C:
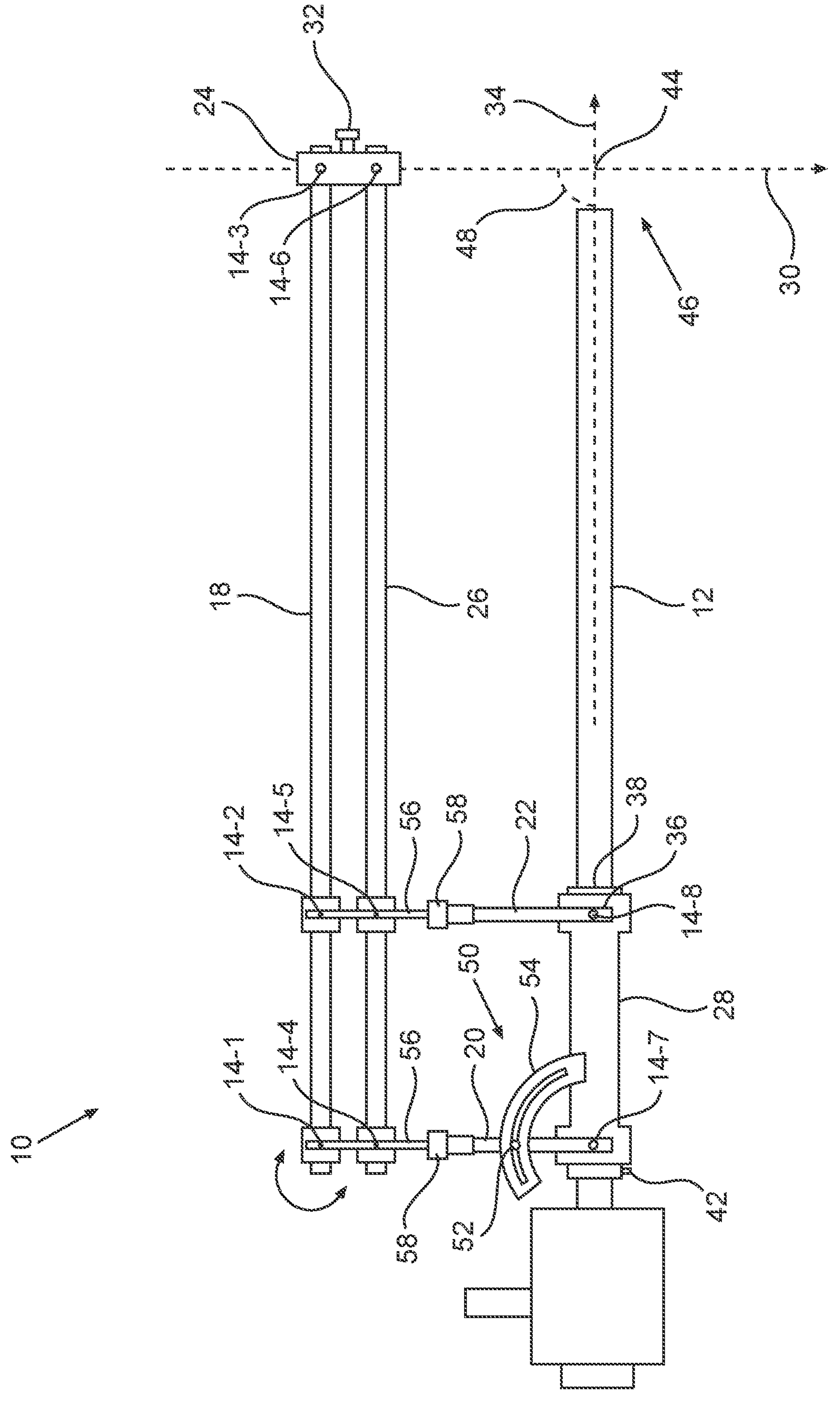
Figure 1D:
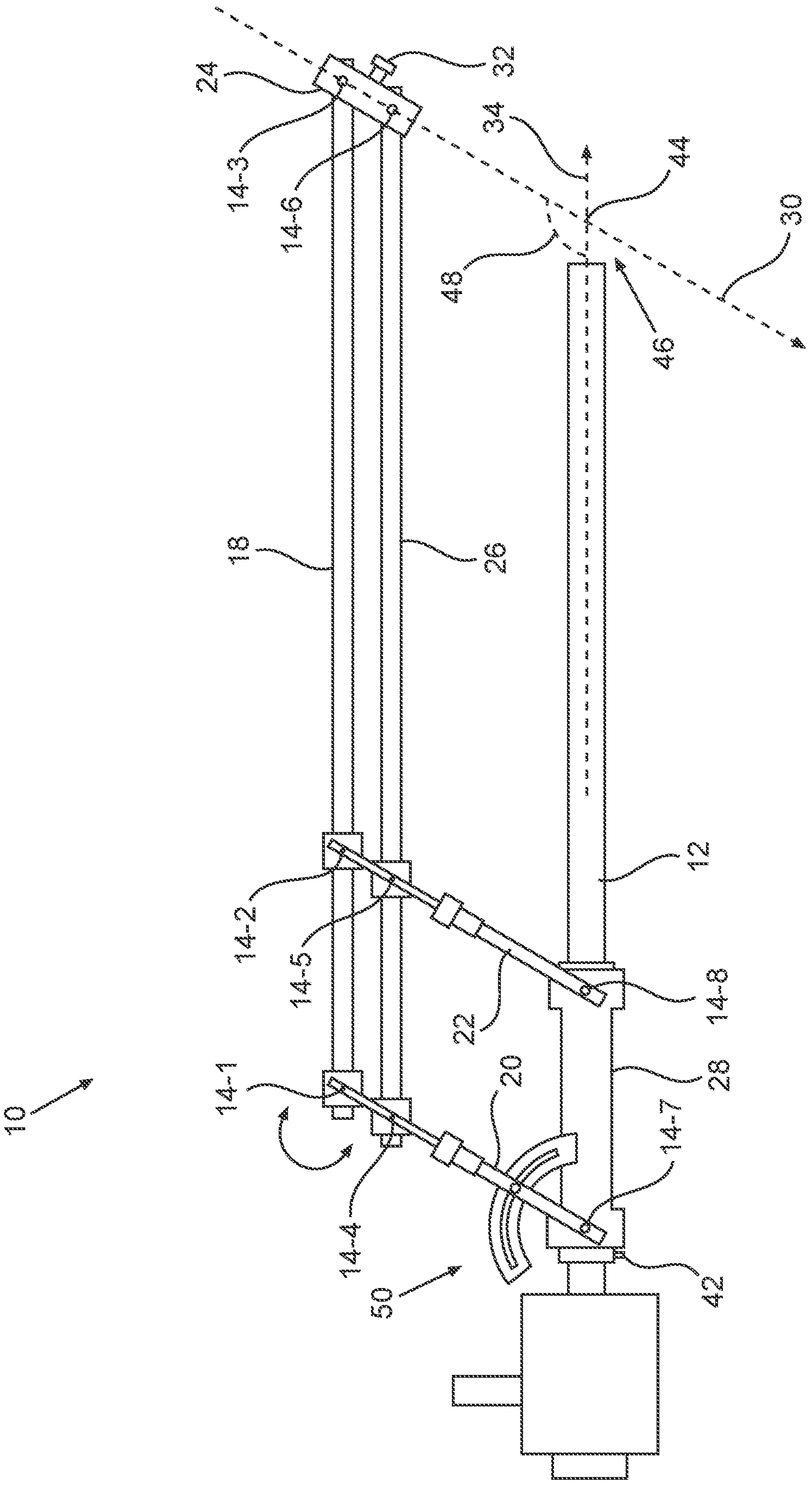

FIGS. 1A to 1D schematically depict a first exemplary embodiment of a guide device according to the teachings herein:

in FIG. 1A in side view in a configuration where the working channel axis is perpendicular to the irrigation channel axis;

in FIG. 1B in view from the back;

in FIG. 1C in side view with a physically associated irrigation channel 12 in a conformation where the working part axis is perpendicular to the irrigation channel axis; and in FIG. 1D in side view with a physically associated irrigation channel 12 in a conformation where the working part axis is not perpendicular to the irrigation channel axis.

The components of device 10 are made of autoclavable surgical stainless steel and spring steel using methods known in the art of surgical instrumentation.

Guide device 10 comprises eight parallel-axis revolute joints 14-*n*, where n is an integer between 1 and 8. As known in the art, each revolute joint has a single degree of freedom, rotation around a respective joint axis 16, which in device 10 is defined by a stainless steel pin. The joint axes 16 of all eight revolute joints 14-*n* are parallel, in FIGS. 1A, 1C and 1D being perpendicular to the sheet and in FIG. 1B being horizontal to the sheet. In device 10, all eight revolute joints 14-*n* are coplanar, that is to say, there exists a plane perpendicular to the joint axes 16 that intersects all of the joints 14-*n*.

Guide device 10 further comprises four rigid linkages linking the eight revolute joints 14-*n* and two channel holders one to the other:

Link 1 of 4 a rigid upper working channel link 18 connected to:

a rigid proximal transmission link 20 (in device 10, made of two separate bars 20*a* and 20*b*) with a first revolute joint 14-1, a rigid distal transmission link 22 (in device 10, made of two separate bars 22*a* and 22*b*) with a second revolute joint 14-2, and a working channel holder 24 with a third revolute joint 14-3;

Link 2 of 4 a rigid lower working channel link 26 connected to:

proximal transmission link 20 with a fourth revolute joint 14-4, rigid distal transmission link 22 with a fifth revolute joint 14-5, and working channel holder 24 with a sixth revolute joint 14-6;

Link 3 of 4 rigid proximal transmission link 20 connected to an irrigation channel holder 28 with a seventh revolute joint 14-7; and Link 4 of 4 rigid distal transmission link 22 connected to irrigation channel holder 28 with an eighth revolute joint 14-8.

Working channel holder 24 defines a working channel axis 30. Working channel holder 24 is a component configured to reversibly hold a cannula suitable for use as a working channel for TMJ arthroscopy so that the held cannula is substantially coaxial with working channel axis 30. Axes of rotation 16 of revolute joints 14-*n* are substantially perpendicular to a plane that includes working channel axis 30. In device 10, working channel holder 24 comprises a rectangular block/body of stainless steel that is connected to both the third and sixth revolute joints 14-3 and 14-6 so that working channel holder 24 directly rigidly connects third and sixth revolute joints 14-3 and 14-6. Passing through the block/body of steel is a cylindrical hole (not depicted) coaxial to working channel axis 30, the cylindrical hole configured to accept a cannula suitable for use as a working channel for TMJ arthroscopy. Functionally associated with working channel holder 24 is a working channel lock 32, a thumb screw, configuring to reversibly secure a held working channel to working channel holder 24. For use, a suitable cannula is threaded through the cylindrical hole of working channel holder 24, and then working channel lock 32 is rotated so that the distal end of the thumb screw presses against the wall of the working channel, thereby holding the working channel fixedly in place and directed along working channel axis 30.

Irrigation channel holder 28 defines an irrigation channel axis 34. irrigation channel holder 28 is a component configured to reversibly hold a cannula suitable for use as an irrigation channel for TMJ arthroscopy so that the held cannula is substantially coaxial with irrigation channel axis 34. Axes of rotation 16 of revolute joints 14-*n* are substantially perpendicular to a plane that includes irrigation channel axis 34. Additionally, axes of rotation 16 of revolute joints 14-*n* are perpendicular to a plane that includes both working channel axis 30 and irrigation channel axis 34. irrigation channel holder 28 of device 10 is also configured to allow rotation around the irrigation channel axis 34 of a working channel 12 held therein relative to the rest of device 10. Specifically, irrigation channel holder 28 is made of two steel cylinders both coaxial with irrigation channel axis 34: an outer sleeve 36 that is connected to both seventh and eighth revolute joints 14-7 and 14-8 and an inner sleeve 38 that is rotatably mounted inside the bore of outer sleeve 36 with the help of roller bearings (not depicted). Inner sleeve 38 further includes a cylindrical hole 40 configured to accept a cannula suitable for use as an irrigation channel for TMJ arthroscopy such as 12. Functionally associated with irrigation channel holder 28 is an irrigation channel lock 42, a thumb screw, configuring to reversibly secure a held irrigation channel to irrigation channel holder 28.

Working channel axis 30 and irrigation channel axis 34 substantially intersect at an intersection 44 that is within a specific empty volume 46. By "substantially intersect" is meant that in some embodiments, the size of the intersection of a working channel axis and of an irrigation channel axis is such that the working channel axis and the irrigation channel axis pass within a distance of not more than 10 mm one from the other. In some embodiments, the distance is not more than 7 mm, not more than 3 mm and even not more than 1 mm.

Upper working channel link 18, lower working channel link 26 and irrigation channel axis 34 are parallel. Proximal transmission link 10, distal transmission link 22 and working channel axis 30 are parallel. Therefore, revolute joints 14-*n*, upper working channel link 18, lower working channel link 26, irrigation channel holder 28, irrigation channel axis 34, proximal transmission link 20, distal transmission link 22, working channel holder 24, working channel axis 30 and together define three linked parallelograms, each of the three parallelograms having sides with fixed lengths but changeable angles.

In device 10, a first parallelogram is associated with working channel holder 24, having four vertices defined by four real revolute joints:

first revolute joint 14-1, third revolute joint 14-3, fourth revolute joint 14-4, and sixth revolute joint 14-6, and four sides defined by four linkages:

upper working channel link 18, lower working channel link 26, proximal transmission link 20 and working channel holder 24.

In device 10, a second parallelogram is associated with irrigation channel holder 28, having four vertices defined by four real revolute joints:

first revolute joint 14-1, second revolute joint 14-2, seventh revolute joint 14-7, and eighth revolute joint 14-8, and four sides defined by four linkages:

upper working channel link 18, irrigation channel holder 28, proximal transmission link 20 and distal transmission link 22.

In device 20, a third parallelogram is associated with intersection 44, having four vertices, of which three are real revolute joints:

first revolute joint 14-1, third revolute joint 14-3, seventh revolute joint 14-7, and intersection 44, and four sides defined by four linkages:

upper working channel link 18, irrigation channel axis 34 which is an extension of irrigation channel holder 28, proximal transmission link 20 and working channel axis 30 which is an extension of working channel holder 24.

Each pair of the three parallelograms shares at least one real side and at least one revolute joint physically connected thereto so that the rotation of revolute joints 14-*n* around the respective axes is linked. In device 10, all three parallelograms share the same real side (upper working channel link 18) and the same revolute joint connected thereto (first revolute joint 14-1).

At intersection 44, working channel axis 30 and irrigation channel axis 34 intersect at an intersection angle 48. Intersection angle 48 is changeable by rotation of revolute joints 14-*n*, that is to say, movement of the device components around revolute joints 14-*n*. Due to the linked-parallelogram arrangement of the components, such rotation of revolute joints 14-*n* does not substantially change the distance of intersection 44 relative to third revolute joint 14-3 (and consequently relative to a working channel held in working channel holder 24) or relative to seventh revolute joint 14-7 (and consequently relative to an irrigation channel held in irrigation channel holder 28). As a result and as detailed hereinbelow, the user of a device according to the teachings herein, such as device 10, is able to insert both an irrigation channel 12 and a working channel into a TMJ joint with confidence that the distal tips thereof are properly located to perform TMJ arthroscopy, with an intersection angle 48 that is optionally different from 90° if the user of the device so desires. The action of the linked parallelograms during rotation of revolute joints 14-*n* can be better understood by comparing FIG. 1C to FIG. 1D.

In FIG. 1C, device 10 is depicted in a conformation where the sides of the parallelograms are perpendicular one to the other so that intersection angle 48 is 90°.

When upper working channel link 18 is pushed forwards while irrigation channel holder 28 is held in place, the linked parallelograms skew, as depicted in FIG. 1D. As a result of the linkage between the parallelograms, all revolute joints 14-*n* rotate the same degree so that the sides of the parallelograms intersect at the same non-90° angle, including intersection angle 48 but the location of intersection 44 relative to irrigation channel holder 28 and remains unchanged.

As described elsewhere herein, arthroscopy is performed by insertion of a viewing tool (e.g., an endoscope) from one aperture (e.g., the irrigation aperture) and insertion of a working tool via a second aperture (e.g., the working aperture) so that the procedure is carried out while viewing the working tool via the viewing tool. Oftentimes, inter-procedure manipulation of the working tool causes the distal portion of the tool to exit the field of view (FOV) of the viewing tool. In TMJ surgical procedures, this may mean a necessity to re-puncture the joint capsule which, as explained elsewhere herein, is undesirable.

Figure 8A:
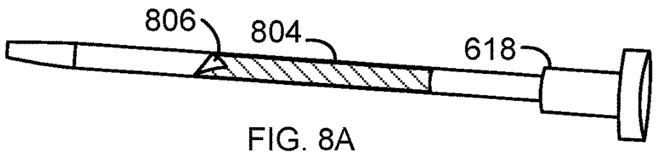
FIGS. 8A, 8B, 8C, 8D and 8E are oblique view and cross-section view simplified illustrations of employment of a gripping patch in accordance with some embodiments of the invention.
Figure 8B:
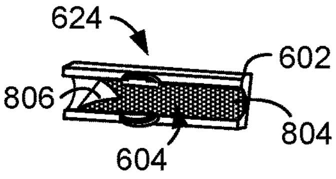

A potential advantage in the unchanged location of intersection 44 relative to irrigation channel holder 28 while manipulating, expanding or retracting guide device (10, 60, 62, 68, 70, 72, 74, 500) is in that an end portion (e.g., a tip) of the working tool remains within an FOV of the viewing tool throughout the procedure. Additionally, and optionally, in some embodiments, one or more holding channels (24/28, 510/512, 624) comprises a cannula insertion limiter 812 (FIG. 8B). In some embodiments, cannula insertion limiter 812 comprises an ergonomic locking screw. In some embodiments, cannula insertion limiter 812 comprises a ball and detent system 814 wherein the ball is configured to fit in notches 816 made in a wall of a working cannula at predetermined distances.

In some embodiments, device 10 further comprises a rotation lock 50 allowing reversible fixing of an angle of rotation of revolute joints 14-*n*, that is to say, allows fixing of a specific conformation of the device. In device 10, rotation lock 50 comprising a locking pin 52 (e.g., similar to a locking pin made by CarrLane Manufacturing Co., St. Louis Mo., USA) and a locking rail 54. When locking pin 52 is in a disengaged state, locking pin 52 travels freely in locking rail 54 as the various components of device 10 are rotated around revolute joints 14-*n* as described above, allowing a user to select a desired intersection angle 48. When a desired intersection angle 48 is attained, locking pin 52 is moved to an engaged state, preventing further rotation of the components of device 10 around revolute joints 14-*n*.

Use of Device 10

Performance of TMJ arthroscopy with the assistance of a device according to the teachings herein, such as device 10, is clear to a person having ordinary skill in the art upon perusal of the teachings herein. An exemplary embodiment of a device according to the teachings herein is described with reference to device 10.

A first cannula suitable for use as an irrigation channel 12 for TMJ is associated with a device 10 through irrigation channel holder 28 and secured thereto with the help of irrigation channel lock 42.

The first cannula is associated with a trocar in the usual way and pushed through the skin and other tissue to enter the TMJ. Once the distal tip of the cannula is properly positioned so as to constitute an irrigation channel, the trocar is withdrawn, fluid such as saline is pumped through the irrigation channel in the usual way into the TMJ to cause hydrodistension of the TMJ, forming a relatively large fluid-filled space.

A second cannula suitable for use as a working channel for TMJ is associated with device 10 through working channel holder 24. While working channel lock 32 is free (so that the second cannula can be moved back and forth along working channel axis 30 in working channel holder 42) and locking pin 52 is disengaged (allowing device 10 to be skewed and thereby intersection angle 48 to be adjusted), the user positions the distal tip of the trocar associated with the second cannula as desired by moving the second cannula back and forth along working channel axis 30), by skewing device 10 to adjust intersection angle 48 and by rotating device 10 around irrigation channel axis 34 without moving the irrigation channel.

When a desired entry point and angle is found, the user pushes the second cannula through the skin and other tissue to enter the TMJ with absolute confidence that the distal tip of the second cannula will be properly positioned inside the fluid-filled space.

The trocar is withdrawn and the actual TMJ arthroscopy is then performed.

When the TMJ arthroscopy is complete, the two channels are withdrawn. All other things being equal, the procedure is less traumatic than prior known TMJ procedures because placement of the channels is quick and accurate.

Adjustable-Length Transmission Links

In device 10, the length of both proximal transmission link 20 and distal transmission link 22 is adjustable, allowing an operator to change the "height" of device 10, for example to account for the size of the jaw of a subject undergoing a TMJ arthroscopy. Specifically, both proximal transmission link 20 and distal transmission link 22 include a telescopic screw 56. When a nut 58 of telescopic screw 56 is rotated in one direction, the respective link becomes longer; when nut 58 is rotated in the opposite direction, the respective link becomes shorter.

Working Channel Holder

A working channel holder of a guide device according to the teachings herein is any component suitable for holding a suitable cannula to constitute a working channel for TMJ arthroscopy. Although other working channel holder constructions may be used to implement the teachings herein, in device 10, working channel holder 24 comprises a cylindrical hole through which a suitable cannula can be slidingly moved back and forth along working channel axis 30 to constitute a working channel. As described above, in some embodiments, the working channel holder is configured for reversibly holding a working channel. In some embodiments, a working channel holder is configured for permanently holding a working channel, for example, the working channel holder is a component of the working channel.

As described above, in some embodiments a guide comprises a working channel lock for reversibly securing a working channel held therein, allowing a user to optionally secure a held working channel to prevent sliding of the held working channel along the working channel axis. In some embodiments, a guide device is devoid of a working channel lock. In preferred embodiments, a device according to the teachings herein comprises a working channel lock such as working channel lock 32 of device 10. Any suitable working channel lock may be used for implementing the teachings herein. In the embodiments described above, a working channel is held in working channel holder 24 using a thumb screw as a working channel lock 32. Other suitable such working channel lock mechanisms include elastic components such as leaf springs and garter springs deployed inside a cylindrical hole; matching screw threads on a cylindrical hole/working channel; bayonet connectors; and a multi-part working channel holder configured to grip a respective working channel as explained in greater detail elsewhere herein.

Irrigation Channel Holder

An irrigation channel holder of a guide device according to the teachings herein is any component suitable for holding a suitable cannula to constitute an irrigation channel for TMJ arthroscopy. Although other irrigation channel holder constructions may be used to implement the teachings herein, in device 10 depicted above, an irrigation channel holder 24 comprises a cylindrical hole of inner sleeve 38 through which a suitable cannula is threaded to constitute an irrigation channel. As described above, in some embodiments, the irrigation channel holder is configured for reversibly holding an irrigation channel. In some embodiments, an irrigation channel holder is configured for permanently holding an irrigation channel, for example, the irrigation channel holder is a component of the irrigation channel.

As described above, in some embodiments a guide comprises an irrigation channel lock for reversibly securing an irrigation channel held therein, allowing a user to optionally secure a held irrigation channel to prevent sliding of the held irrigation channel along the irrigation channel axis. In some embodiments, a device is devoid of an irrigation channel lock. In preferred embodiments, a device according to the teachings herein comprises an irrigation channel lock such as irrigation channel lock 42 of device 10. Any suitable irrigation channel lock may be used for implementing the teachings herein. In the embodiments described above, an irrigation channel is held in irrigation channel holder 28 using a thumb screw as an irrigation channel lock 42. Other suitable such irrigation channel lock mechanisms include elastic components such as leaf springs and garter springs deployed inside a cylindrical hole; matching screw threads on a cylindrical hole/working channel; bayonet connectors; and multi-part irrigation channel holders configured to grip a respective irrigation channel as explained in greater detail elsewhere herein.

Second Embodiment of the Device

Figure 2:
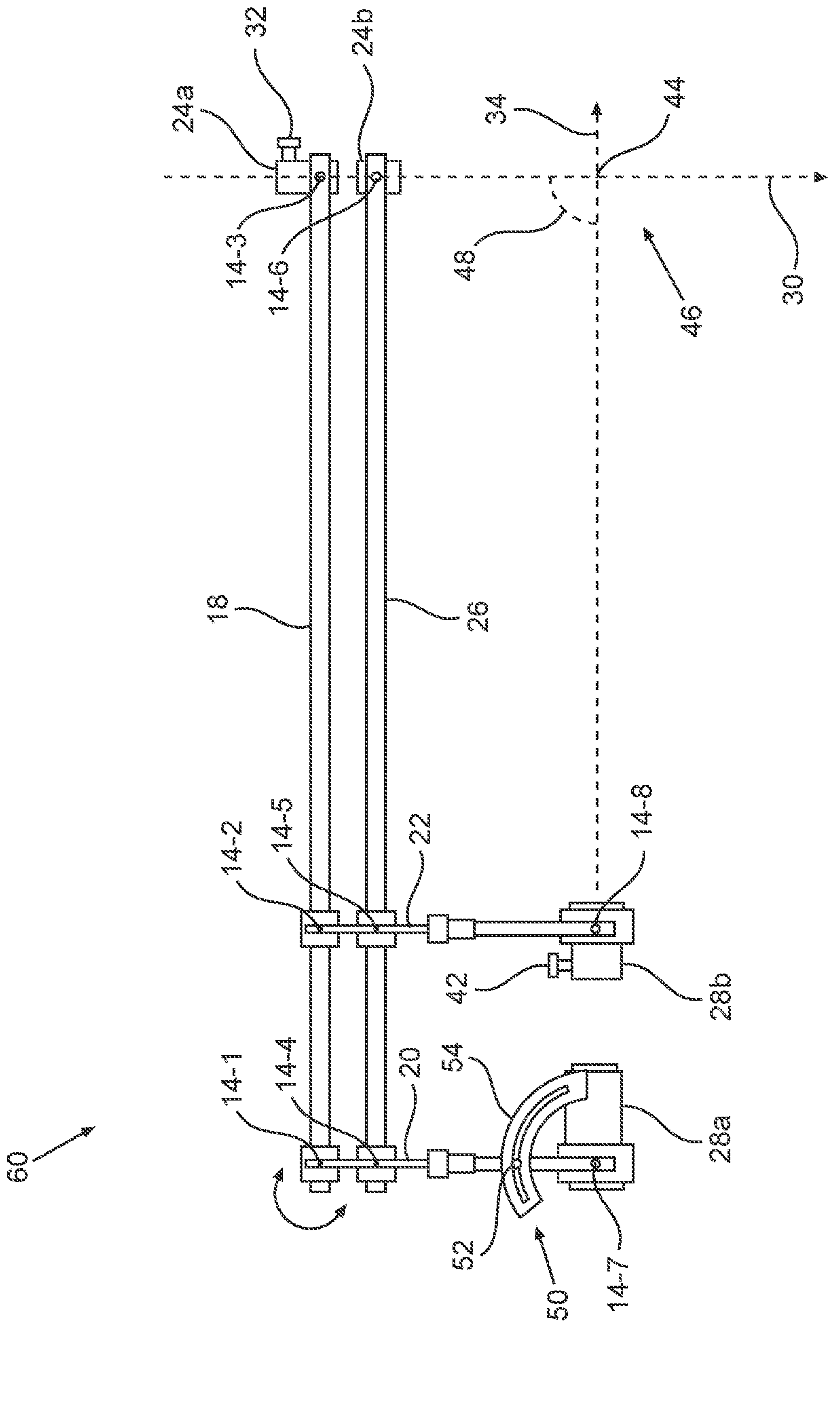
FIG. 2 depicts a second exemplary embodiment of a guide device according to the teachings herein having a two-part working channel holder and a two-part irrigation channel holder in side view.

A second exemplary embodiment of a guide device according to the teachings herein, device 60, is schematically depicted in FIG. 2 in side view. Most of the components and construction, as well as the use of device 60 are substantially the same as of device 10 so for the sake of brevity will not be discussed further.

A notable difference between device 60 and device 10 is the construction of working channel holder 24 and of irrigation channel holder 28.

In device 10, working channel holder 24 directly rigidly connects the third and sixth revolute joints 14-3 and 14-6 respectively, whether or not there is a working channel held therein.

In contrast, in device 60, working channel holder 24 comprises two physically separate working channel holder parts, first part 24*a* connected to third revolute joint 14-3 and second part 24*b* connected to sixth revolute joint 14-6. In device 60, third and sixth revolute joints are directly rigidly connected only when a working channel is held in both parts 24*a* and 24*b*.

Similarly, in device 10, irrigation channel holder 28 directly rigidly connects the seventh and eighth revolute joints 14-7 and 14-8 respectively, whether or not there is an irrigation channel held therein.

In contrast, in device 60, irrigation channel holder 28 comprises two physically separate irrigation channel holder parts, first part 28*a* connected to seventh revolute joint 14-7 and second part 28*b* connected to eighth revolute joint 14-8. In device 60, seventh and eighth revolute joints are directly rigidly connected only when an irrigation channel is held in both parts 28*a* and 28*b*.

Third Embodiment of the Device

Figures 3A, 3B:
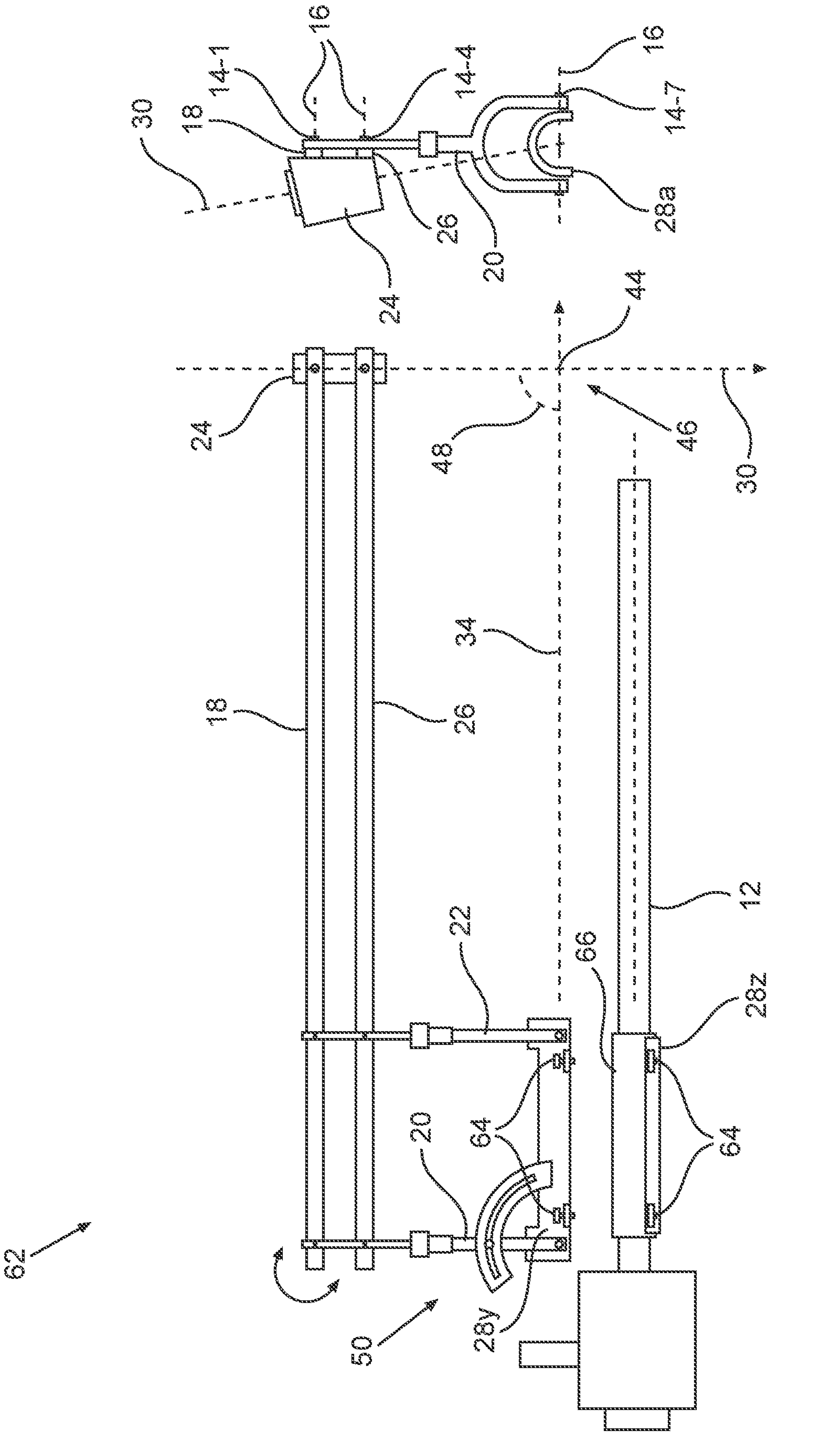
FIGS. 3A to 3B schematically depict a third exemplary embodiment of a guide device according to the teachings herein, wherein axes of rotation of the eight revolute joints are not perpendicular to a plane that includes both the working channel axis and the irrigation channel axis.

A third exemplary embodiment of a guide device according to the teachings herein, device 62, is schematically depicted in FIG. 3A in side view and in FIG. 3B in view from the back. Most of the components and construction, as well as the use, of device 62 are substantially the same as of device 10 so for the sake of brevity will not be discussed further.

A first difference is that device 62 is devoid of a working channel lock.

As noted above, in device 10, axes of rotation 16 of revolute joints 14-*n* are perpendicular to a plane that includes both working channel axis 30 and irrigation channel axis 34.

In contrast, in device 62, although axes of rotation 16 of revolute joints 14-*n* are substantially perpendicular to a plane that includes irrigation channel axis 34, axes of rotation 16 of revolute joints 14-*n* are not perpendicular to a plane that includes both working channel axis 30 and irrigation channel axis 34. In device 62, working channel holder 24 comprises a stainless-steel block/body attached to third and sixth revolute joints 14-3 and 14-6, but offset therefrom. The stainless-steel block/body includes a cylindrical hole passing therethrough, the axis of the cylindrical hole defining working channel axis 30 at an angle of 20° from perpendicular to axes 16 of revolute joints 14-*n*, as depicted in FIG. 3B.

An additional difference between device 10 and device 62 is that irrigation channel holder 28 comprises two parts. Upper irrigation channel holder part 28*y* is attached to revolute joints 14-7 and 14-8 as described above and defines irrigation channel axis 34. Lower irrigation channel holder part 28*z* is a component of irrigation channel 12 and is configured to reversibly attach to upper irrigation channel holder part 28*y* using fasteners 64. Since lower irrigation channel holder part 28*y* is a component of irrigation channel 12, irrigation channel holder 28 of device 62 also functions as an irrigation channel lock. Lower irrigation channel holder 28*y* includes a rotation sleeve 66 that encircles a portion of irrigation channel 12. Between rotation sleeve 66 and the portion of irrigation channel 12 are a plurality of roller bearings, allowing irrigation channel 12 to freely rotate around irrigation channel axis 34 relative to rotation sleeve 66.

An advantage of such a two-part irrigation channel holder is that during use, irrigation channel 12 is pushed through the tissue of a subject to the TMJ without being attached to device 62. Once the distal tip of irrigation channel 12 is properly located inside the TMJ, the rest of device 62 is attached to irrigation channel 62 through upper irrigation channel holder part 28*y* and secured with fasteners 64.

Further Embodiment of the Device

Devices 10, 60 and 62 discussed above have eight revolute joints 14-*n*.

Further exemplary embodiments of a guide device according to the teachings herein, devices 68, 70, 72 and 74 are schematically depicted in FIGS. 4A, 4B, 4C and 4D respectively in side view. Devices 68, 70, 72 and 74 are substantially identical to device 10 except that each one of devices 68, 70, 72 and 74, has only seven real revolute joints, the other revolute joint being virtual. As discussed above with reference to devices 10, 60 and 62, the revolute joints and linkages of devices 68, 70, 72 and 74 define at least three linked parallelograms in accordance with the teachings herein.

Figure 4A:
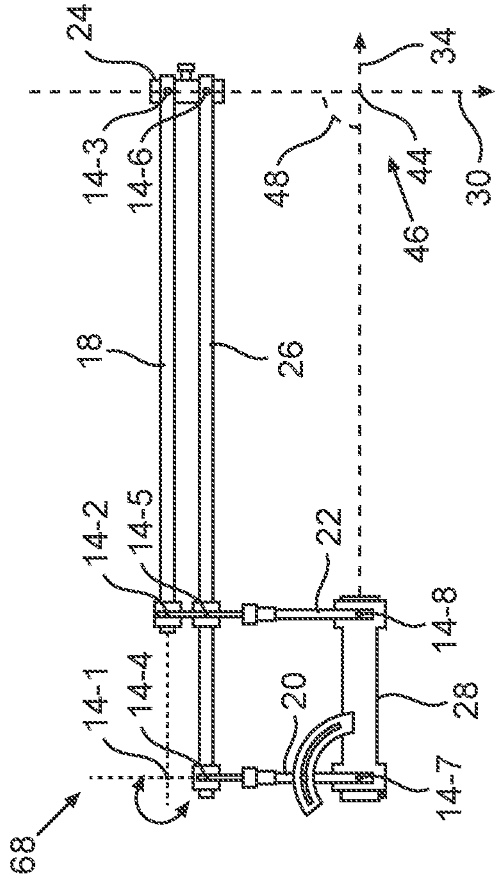
FIGS. 4A to 4D each schematically depicts a different exemplary embodiment of a guide device according to the teachings herein having seven real revolute joints.

Device 68 in FIG. 4A

In device 68 depicted in FIG. 4A, first revolute joint 14-1 is virtual and the seven other revolute joints 14-*n* are real. In device 68, a first parallelogram is associated with working channel holder 24, having four vertices defined by four real revolute joints:

second revolute joint 14-2, third revolute joint 14-3, fifth revolute joint 14-5, and sixth revolute joint 14-6, and four sides defined by four linkages:

upper working channel link 18, lower working channel link 26, distal transmission link 22 and working channel holder 24.

In device 68, a second parallelogram is associated with irrigation channel holder 28, having four vertices defined by four real revolute joints:

fourth revolute joint 14-4, fifth revolute joint 14-5, seventh revolute joint 14-7, and eighth revolute joint 14-8, and four sides defined by four linkages:

lower working channel link 26, irrigation channel holder 28, proximal transmission link 20 and distal transmission link 22.

In device 68, a third parallelogram is associated with intersection 44, having four vertices, of which three are real revolute joints:

fifth revolute joint 14-5, sixth revolute joint 14-6, eighth revolute joint 14-8, and intersection 44, and four sides defined by four linkages:

lower working channel link 26, irrigation channel axis 34 which is an extension of irrigation channel holder 28, distal transmission link 22 and working channel axis 30 which is an extension of working channel holder 24.

Each pair of the three parallelograms shares at least one real side and at least one revolute joint physically connected thereto so that the rotation of revolute joints 14-*n* around the respective axes is linked. In device 68, all three parallelograms share the same real side (lower working channel link 26) and the same revolute joint connected thereto (fifth revolute joint 14-5).

B. Device 70 in FIG. 4B

Figure 4B:
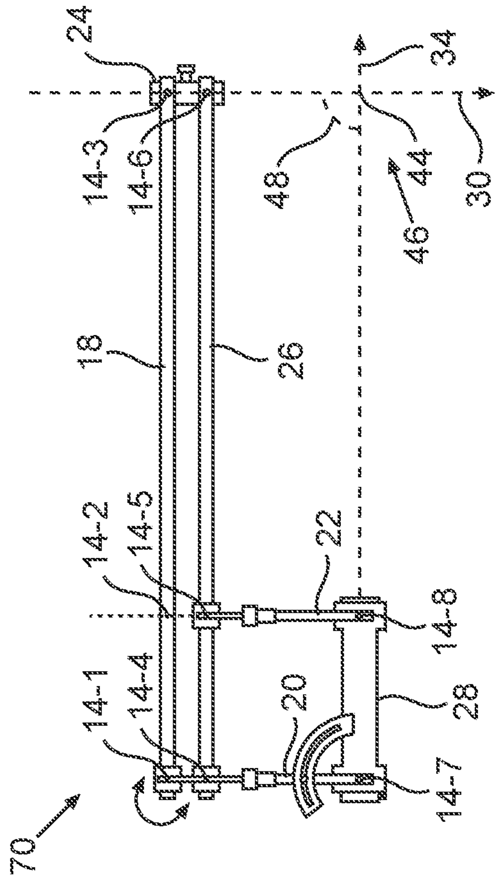

In device 70 depicted in FIG. 4B, second revolute joint 14-2 is virtual and the seven other revolute joints 14-*n* are real. In device 70, a first parallelogram is associated with working channel holder 24, having four vertices defined by four real revolute joints:

first revolute joint 14-1, third revolute joint 14-3, fourth revolute joint 14-4, and sixth revolute joint 14-6, and four sides defined by four linkages:

upper working channel link 18, lower working channel link 26, proximal transmission link 20 and working channel holder 24.

In device 68, a second parallelogram is associated with irrigation channel holder 28, having four vertices defined by four real revolute joints:

fourth revolute joint 14-4, fifth revolute joint 14-5, seventh revolute joint 14-7, and eighth revolute joint 14-8, and four sides defined by four linkages:

lower working channel link 26, irrigation channel holder 28, proximal transmission link 20 and distal transmission link 22.

In device 70, a third parallelogram is associated with intersection 44, having four vertices, of which three are real revolute joints:

fourth revolute joint 14-4, sixth revolute joint 14-6, seventh revolute joint 14-7, and intersection 44, and four sides defined by four linkages:

lower working channel link 26, irrigation channel axis 34 which is an extension of irrigation channel holder 28, proximal transmission link 20 and working channel axis 30 which is an extension of working channel holder 24.

Each pair of the three parallelograms shares at least one real side and at least one revolute joint physically connected thereto so that the rotation of revolute joints 14-*n* around the respective axes is linked. In device 70, all three parallelograms share the same real side (lower working channel link 26) and the same revolute joint connected thereto (fourth revolute joint 14-4).

C. Device 72 in FIG. 4C

Figure 4C:
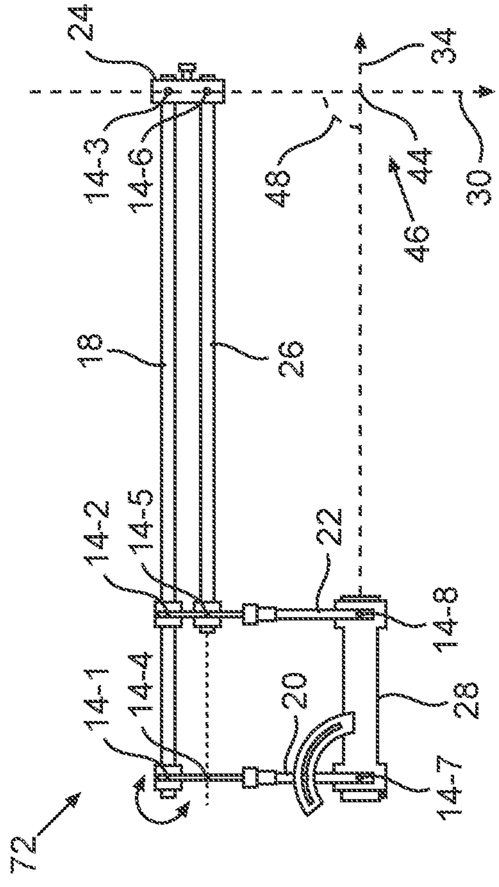

In device 72 depicted in FIG. 4C, fourth revolute joint 14-4 is virtual and the seven other revolute joints 14-*n* are real. In device 72, a first parallelogram is associated with working channel holder 24, having four vertices defined by four real revolute joints:

second revolute joint 14-2, third revolute joint 14-3, fifth revolute joint 14-5, and sixth revolute joint 14-6, and four sides defined by four linkages:

upper working channel link 18, lower working channel link 26, distal transmission link 22 and working channel holder 24.

In device 72, a second parallelogram is associated with irrigation channel holder 28, having four vertices defined by four real revolute joints:

first revolute joint 14-1, second revolute joint 14-2, seventh revolute joint 14-7, and eighth revolute joint 14-8, and four sides defined by four linkages:

upper working channel link 18, irrigation channel holder 28, proximal transmission link 20 and distal transmission link 22.

In device 72, a third parallelogram is associated with intersection 44, having four vertices, of which three are real revolute joints:

second revolute joint 14-2, third revolute joint 14-3, eighth revolute joint 14-8, and intersection 44, and four sides defined by four linkages:

upper working channel link 18, irrigation channel axis 34 which is an extension of irrigation channel holder 28, distal transmission link 22 and working channel axis 30 which is an extension of working channel holder 24.

Each pair of the three parallelograms shares at least one real side and at least one revolute joint physically connected thereto so that the rotation of revolute joints 14-*n* around the respective axes is linked. In device 72, all three parallelograms share the same real side (distal transmission link 22) and the same revolute joint connected thereto (second revolute joint 14-2).

D. Device 74 in FIG. 4D

Figure 4D:
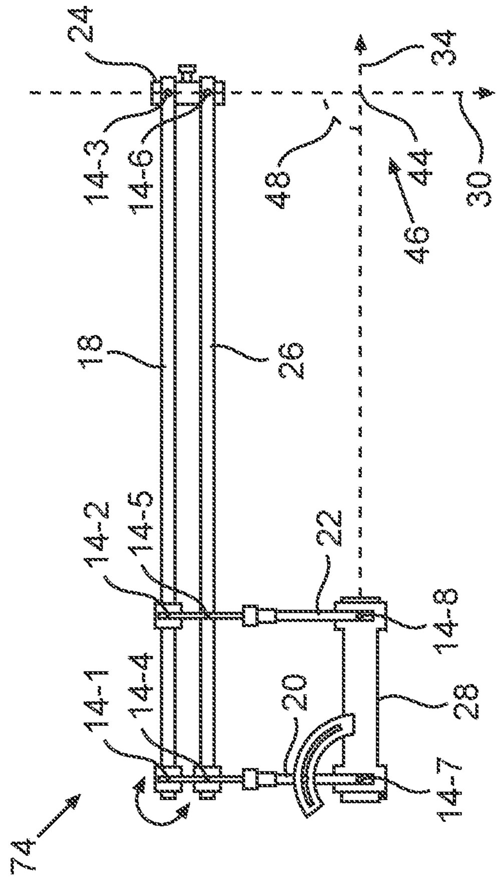

In device 74 depicted in FIG. 4D, fifth revolute joint 14-5 is virtual and the seven other revolute joints 14-*n* are real. In device 74, a first parallelogram is associated with working channel holder 24, having four vertices defined by four real revolute joints:

first revolute joint 14-1, third revolute joint 14-3, fourth revolute joint 14-4, and sixth revolute joint 14-6, and four sides defined by four linkages:

upper working channel link 18, lower working channel link 26, proximal transmission link 20 and working channel holder 24.

In device 74, a second parallelogram is associated with irrigation channel holder 28, having four vertices defined by four real revolute joints:

first revolute joint 14-1, second revolute joint 14-2, seventh revolute joint 14-7, and eighth revolute joint 14-8, and four sides defined by four linkages:

upper working channel link 18, irrigation channel holder 28, proximal transmission link 20 and distal transmission link 22.

In device 74, a third parallelogram is associated with intersection 44, having four vertices, of which three are real revolute joints:

first revolute joint 14-1, third revolute joint 14-3, seventh revolute joint 14-7, and intersection 44, and four sides defined by four linkages:

upper working channel link 18, irrigation channel axis 34 which is an extension of irrigation channel holder 28, proximal transmission link 20 and working channel axis 30 which is an extension of working channel holder 24.

Each pair of the three parallelograms shares at least one real side and at least one revolute joint physically connected thereto so that the rotation of revolute joints 14-*n* around the respective axes is linked. In device 74, all three parallelograms share the same real side (upper working channel link 18) and the same revolute joint connected thereto (first revolute joint 14-1).

The dimensions of a device according to the teachings herein are any suitable dimensions and are primarily dependent on the dimensions of the cannulae to be used as the irrigation channel and the working channel, as well as the dimensions of the subject who is to undergo the TMJ arthroscopy, typically a human, especially a human adult. Accordingly, different embodiments of the device have different dimensions. That said, in some typical embodiments, the distance between the first and the seventh revolute joints (corresponding to the "height" of the device) is not less than 1 cm and not more than 15 cm, more typically not less than 5 cm and not more than 10 cm and the distance between the first and the third revolute joints (corresponding to the "length" of the device) is not less than 5 cm and not more than 20 cm.

In the specific embodiments discussed herein with the figures, the upper working link, the lower working link, the proximal transmission link and the distal transmission link are all depicted as being straight. In some embodiments, one or more of the links is not straight, e.g., curved or crooked.

In the devices discussed above, all eight revolute joints 14-*n* are coplanar, that is to say, there exists a plane perpendicular to the joint axes 16 that intersects all of the joints 14-*n*. In the embodiments, not all eight revolute joints

14-*n* are coplanar, that is to say, there does not exist a plane perpendicular to the joint axes 16 that intersects all of the joints 14-*n*.

Figure 5A:
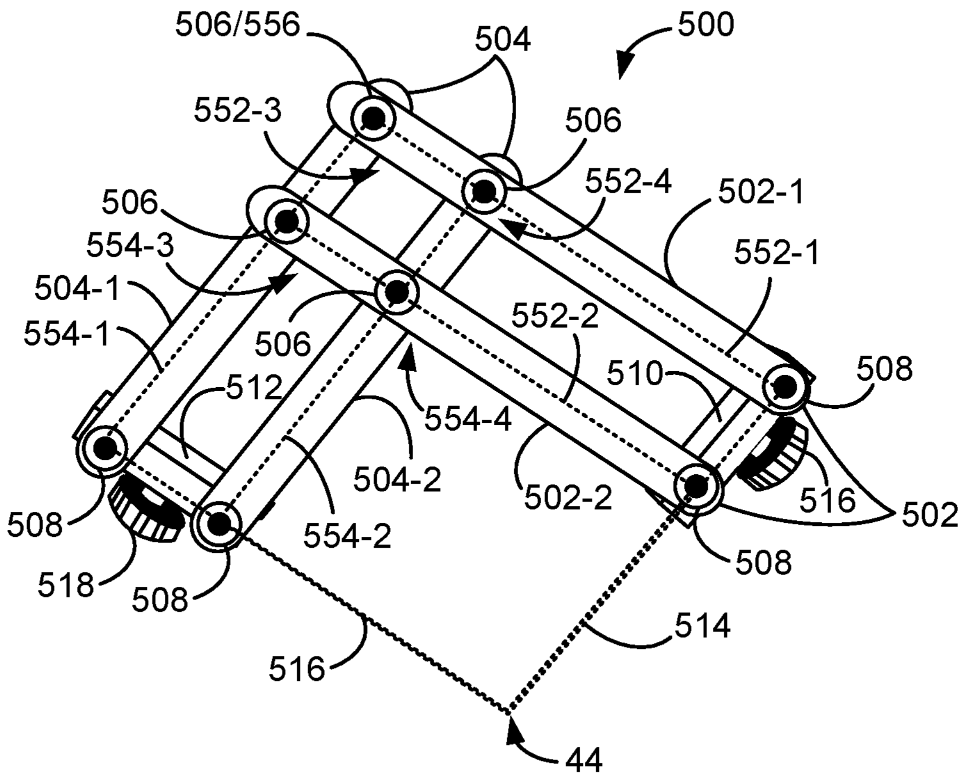
FIGS. 5A and 5B, are side view simplified illustrations of guide devices for TMJ arthroscopy in accordance with some embodiments of the invention.
Figure 5B:
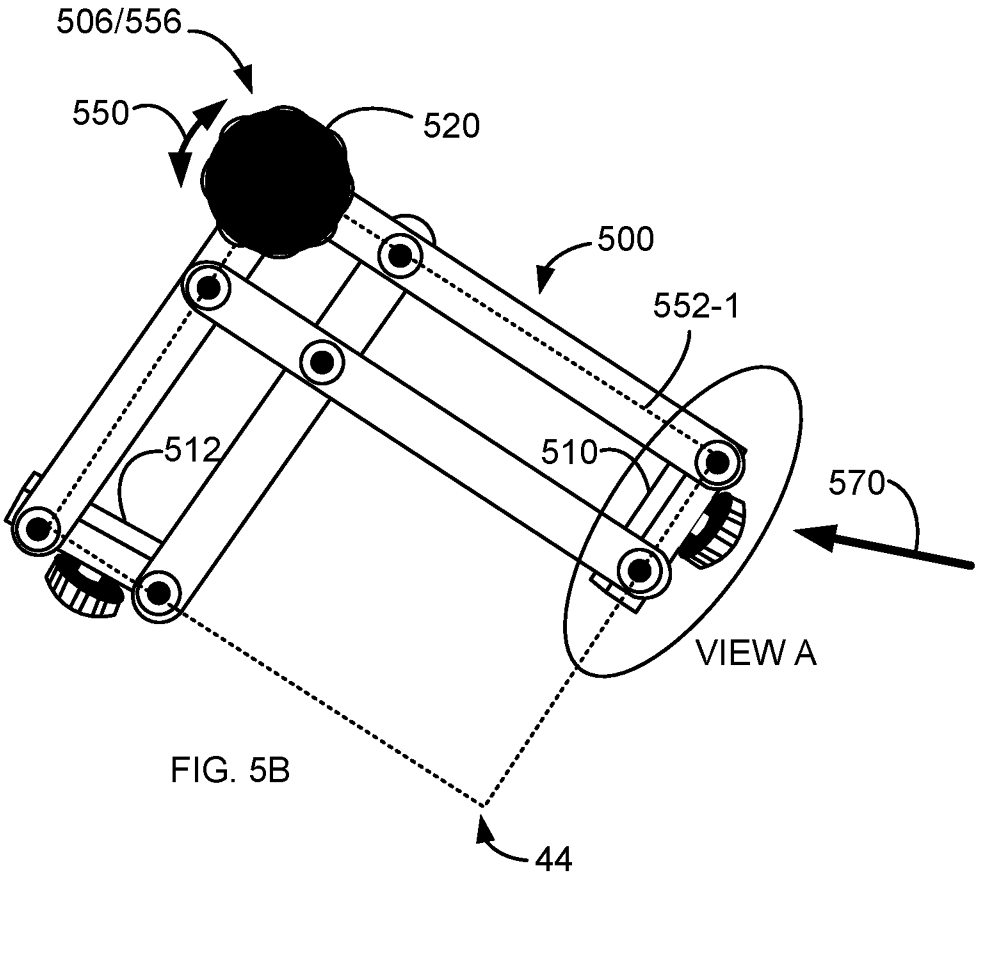

Reference is now made to FIGS. 5A and 5B, which are side view simplified illustrations of guide devices for TMJ arthroscopy in accordance with some embodiments of the invention. As shown in the exemplary embodiment depicted in FIG. 5A, a guide device for TMJ arthroscopy 500 comprises at least two pairs of arms, pair 502 (502-1 and 502-2) and pair 504 (504-1/504-2). In some embodiments, pairs 502 and 504 are pivotly connected via revolute joints 506. In some embodiments, pivot axes of revolute joints 506 are parallel. In the exemplary embodiment shown in FIG. 5A, pairs 502/504 are connected by four parallel-axis revolute joints 506.

In some embodiments, connected pairs 502 and 504 form one or more parallelograms 552-1/552-2 and 554-1/554-2 having arm-connecting revolute joints 506 of connected pairs 502 and 504 located at corresponding vertices 552-3/552-4 and 554-3/554-4 of the corresponding formed parallelograms. In some embodiments, an arm-connecting revolute joint 506 located at a vertex of the largest parallelogram 552-1 comprises a locking joint 556, adjustable from an open-unlocked position that allows adjustment of the device arms to a closed-locked position that fixes the orientation of the arms in respect to each other. In some embodiments, any one of arm-connecting revolute joints 506 may comprise a locking joint 556.

In some embodiments and as explained elsewhere herein, each pair of arms 502/504 is connected at one end thereof to a cannula holder 516/518 via one or more holder-connecting revolute joints 508. E.g., in some embodiments, arm pair 502 is connected at one end to arm pair 504 and at an opposite end to working cannula holder 510. In some embodiments, arm pair 504 is connected at one end to arm pair 502 and at an opposite end to irrigation/viewing cannula holder 512.

In some embodiments, and as explained elsewhere herein, working cannula holder 510 defines a working cannula axis 514 and irrigation/viewing cannula holder 512 defines an irrigation/viewing cannula axis 516 that intersects with working cannula axis 514 at an intersection 44. Intersection 44 and at least and at least arm-connecting revolute joint 506 locking joint 556 are located at opposing vertices of the largest parallelogram 552-1.

A potential advantage in the unchanged location of intersection 44 relative to irrigation channel holder 28 while manipulating, expanding or retracting guide device (10, 60, 62, 68, 70, 72, 74, 500) is in that an end portion (e.g., a tip) of the working tool remains within an FOV of the viewing tool throughout the procedure.

In some embodiments, and as explained in greater detail elsewhere herein, cannula holders 510/512 comprise a cannula channel holder comprising a groove and a cover lockable by a channel cover lock 518.

As shown in FIG. 5A, in some embodiments, guide device for TMJ arthroscopy 500 comprises an ergonomic handle 520. Ergonomic handle 520 and intersection 44 are located at opposing vertices of the largest parallelogram 552-1 positioning ergonomic handle 520 so that to provide control throughout a procedure of the spatial orientation of both cannulae gripped by irrigation/viewing cannula holder 512 and working cannula holder 510. In some embodiments, ergonomic handle 520 is adjustable (e.g., rotatable) to lock/unlock locking joint 556 as indicated by double headed arrow 550. In some embodiments, ergonomic handle 520 comprises a quick-release actuator to lock/unlock locking joint 556. In some embodiments, and as shown in the exemplary embodiment shown in FIG. 8B, guide device for TMJ arthroscopy 500 ergonomic handle 521 is lever-shaped and including finger indentations 818.

Figure 6A:
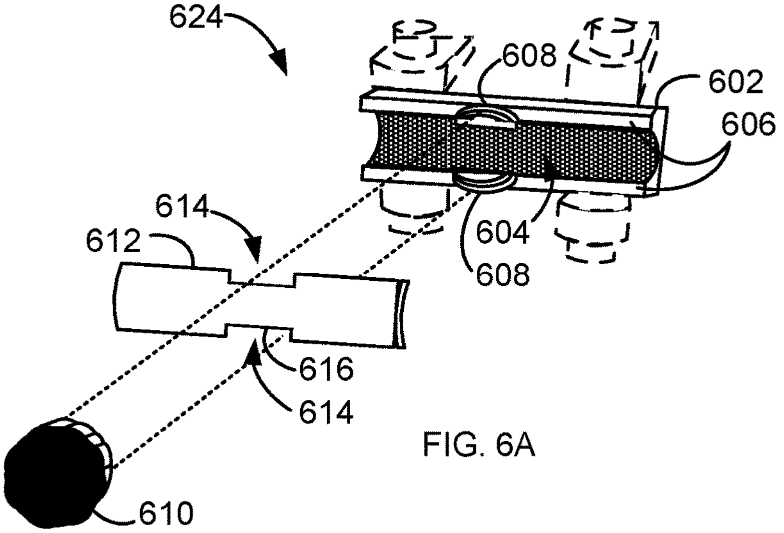
FIG. 6A and FIG. 6B are an exploded view simplified illustration of a guide device cannula channel holder and a perspective view simplified illustration of implementation of a guide device cannula channel holder in accordance with some embodiments of the invention.
Figure 6B:
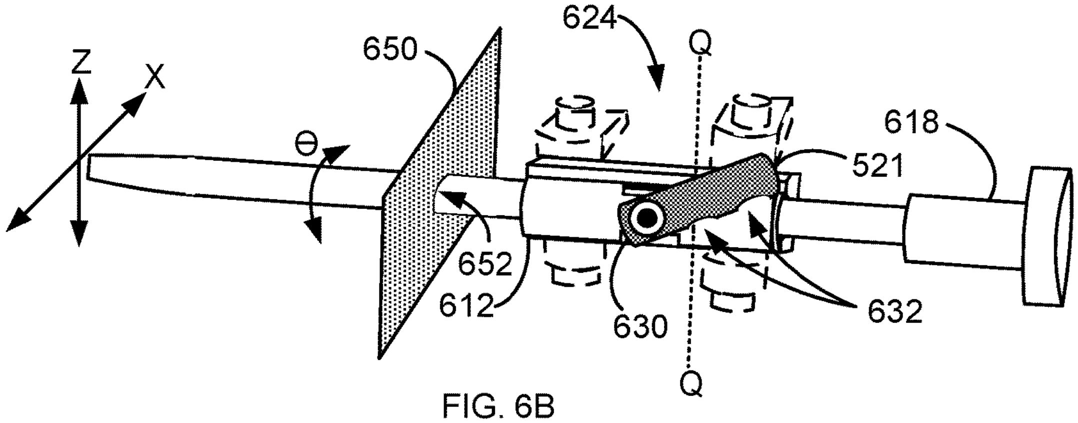

Reference is now made to FIG. 6A, which is an exploded view simplified illustration of a guide device cannula channel holder and FIG. 6B, which is a perspective view simplified illustration of implementation of a guide device cannula channel holder, viewed from a direction indicated in FIG. 5B by an arrow 570, and in accordance with some embodiments of the invention. As shown in the exemplary embodiment depicted in FIG. 6A, in some embodiments, cannula channel holder 624 comprises a body 602 having a furrow 604 longitudinally cut within a surface 606 of body 602. Body 602 surface 606 comprises at least two diametrically opposed portions of a screw thread 608 arranged on opposite edges of furrow 604, configured to receive a threaded bore (not shown) of a locking nut 610. In some embodiments, locking nut 610 comprises a wheel for easy threading of locking nut 610 over diametrically opposed portions of a screw thread 608. In some embodiments, locking nut 610 comprises a quick-release actuator 630 to lock/unlock locking nut 610. In some embodiments, the quick-release actuator 630 is lever-shaped and includes finger grips 632. A potential advantage in a quick-release actuator is in that the actuator does not comprise detachable components increasing safety of guide device 500 in mid-procedure.

In some embodiments, channel holder 624 comprises a furrow cover 612. In some embodiments, furrow cover 612 comprises one or more opposed cutouts 614 that define a furrow cover 612 neck 616 configured to slide in between opposed portions of a screw thread 608. In some embodiments, threading locking nut 610 over opposed portions of a screw thread 608 urges furrow cover 612 closer to furrow 604 and against an instrument (e.g., a cannula) placed between furrow 604 and furrow cover 612.

FIG. 6B shows an embodiment of implementation of channel holder 624. As shown in the exemplary embodiment depicted in FIG. 6B, a cannula 618 is positioned inside furrow 604 and locking nut 610 is threaded over opposed portions of a screw thread 608 urging furrow cover 612 closer to furrow 604 and against cannula 618. A portion 620 of cannula 618 is shown to have penetrated skin 650 forming an aperture 652 to come to rest inside the TMJ joint (not shown). In this state, cannula 618 comprises an operating channel (e.g., irrigation channel, viewing channel and/or working channel) for the arthroscopic procedure.

When carrying out the arthroscopy procedure, the surgeon requires an ability to manipulate a working device inserted via the working channel. Hence, channel holder 624 is configured to maintain retention of the working device in the working channel (e.g., a cannula) and to still allow one or more degrees of movement freedom in 3D space in at least one of Z, X and Θ directions. In some embodiments and optionally, the one or more degrees of movement freedom in 3D space include axial movement of the working device as well. In some embodiments, such movements allow a surgeon to operate the working tool within the FOV of the viewing tool without losing retention of the working tool by working channel holder 510. In some embodiments and optionally, the one or more degrees of micromovement freedom in 3D space include axial movement of the working device as well.

Figures 7A, 7B, 7C:
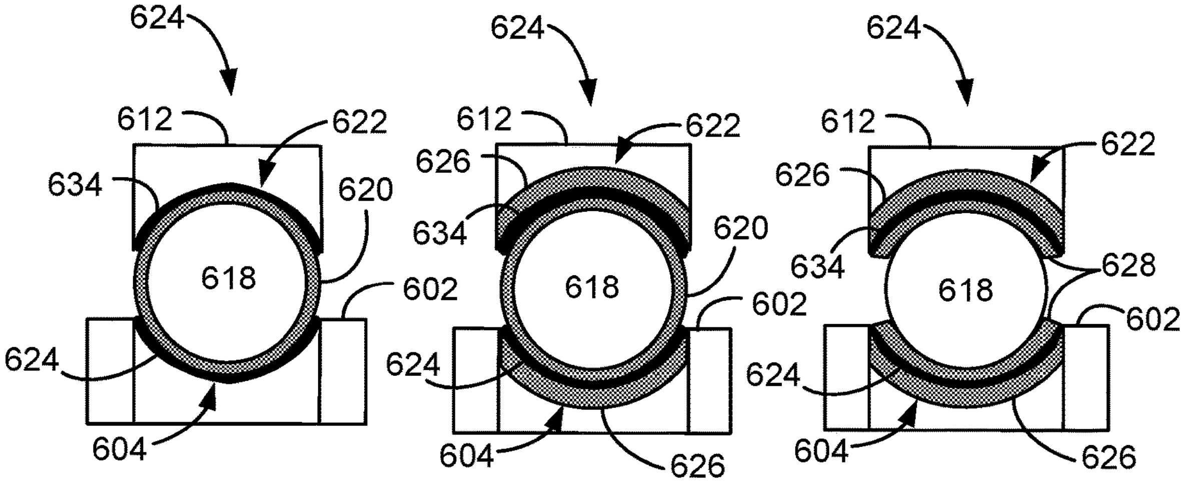
FIGS. 7A, 7B and 7C are cross-section view simplified illustrations of an instrument inside a guide device channel holder in accordance with some embodiments of the invention.

Reference is now made to FIGS. 7A-7C which are cross-section view simplified illustrations taken along axis Q-Q (FIG. 6B) of an instrument (e.g., a cannula) inside channel holder 624 and in accordance with some embodiments of the invention. In some embodiments and as shown in FIG. 7A, a resilient sleeve 620 (e.g., rubber, Silicone or Polyurethane of low shore grades) is fitted over at least a portion of a cannula 618 to provide cushioning to cannula 618 as well as protection from clamping forces applied by furrow 604 and furrow cover 612 when locking nut 610 is tightened.

In some embodiments, resilient sleeve 620 allows one or more degrees of movement freedom in 3D space of cannula 618 while maintaining a retentive quality.

In some embodiments, a surface of furrow 604 and/or an inner surface (cannula 618 contacting surface 622) of furrow cover 612 comprise a layer of a high-friction-coefficient material 634. A potential advantage of a combination of a resilient material (e.g., rubber, Silicone or Polyurethane of low shore grades) and a high-friction-coefficient material is in that the combination provides one or more of cushioning to cannula 618 and protection from clamping forces applied by furrow 604 and furrow cover 612 when locking nut 610 is tightened. In some embodiments, the resilient material (e.g., rubber, Silicone or Polyurethane of low shore grades) comprises a high-friction-coefficient surface (e.g., mechanically formed). In some embodiments, the resilient material (e.g., rubber, Silicone or Polyurethane of low shore grades) is coated with a retentive (e.g., sticky) material.

A potential advantage of a combination of resilient material (e.g., rubber, Silicone or Polyurethane of low shore grades) and a material having a high friction coefficient is in that the combination provides one or more degrees of movement freedom in 3D space of cannula 618 and/or a distal end 806 of a working tool 802 (FIGS. 8A and 8B) and a reduction in clamping pressure necessary to hold cannula 618 while maintaining retentivity of channel holder 624.

As shown in FIG. 7B, in some embodiments, a second layer 626 of a resilient material (e.g., rubber, Silicone or Polyurethane of low shore grades) is provided between high-friction-coefficient material 634 and furrow 604 and/or between high-friction-coefficient material 634 and inner (cannula 618 contacting) surface 622 of furrow cover 612. The addition of a second cushioning layer 626 enhances the cushioning, freedom of movement as well as retentivity of channel holder 624.

In some embodiments, and as depicted in FIG. 7C, high-friction-coefficient material 634 in furrow 604 and/or cannula 618 contacting surface 622 of furrow cover 612 is sandwiched between at least two layers of cushioning layers 626 and 628 (e.g., rubber, Silicone or Polyurethane of low shore grades).

A potential advantage of this configuration is in that cannula 618 is "bare" and is devoid of any added materials (e.g., a resilient sleeve 620) while maintaining cushioning of cannula 618 as well as protection from clamping forces applied to cannula 618 by furrow 604 and furrow cover 612 when locking nut 610 is tightened. A potential advantage of this configuration is in that is provides cannula 618 one or more degrees of movement freedom in 3D space. Additionally, a potential advantage of a combination of a resilient material (e.g., rubber, Silicone or Polyurethane of low shore grades) and a material having a high friction coefficient is in that such a combination provides one or more degrees of movement freedom in 3D space of cannula 618 and/or a distal end 806 of a working tool 802 (FIGS. 8A and 8B) and a reduction in clamping pressure necessary to hold cannula 618 while maintaining retentivity of channel holder 624. The grip of both cannulae (working cannula and irrigation cannula) in the cannula holder of the guide device is achieved by a high friction interface created by the contact of two different surfaces. One surface is made of soft material such as rubber, silicone or polyurethane of low shore grades, and the other an abraded surface. The high friction interface achieves excellent retention of the cannulae without the need to apply high pressure. Both the soft surface and abraded surfaces may be made as a single-use gripping patch, further described herein below that the surgeon applies around the cannula and into the cannula holder. The surfaces can be used interchangeably, meaning that if the surface of the gripping patch that is on the cannula is soft, then the gripping patch on the cannula holder is abraded, and vice versa another embodiments of the high friction interface may comprise the abrading of the metallic inner surface of the cannula holder or cannula by an abrading tool.

In addition to high friction, retention and grip, the high friction interface is configured to allow minimal movements of the cannula in the cannula holder along a 360° angle, while the cannula (irrigation or working) is maintained fixed in the cannula holder to a certain depth. Said movements are facilitated by the force applied by the user against the soft surface (i.e. by squeezing/squashing). Said movements are affected by two factors, the rigidity and the width of the soft surface. Said movements are essential for the surgical functions and keeping the tools within the FOV (i.e. minimal-movements of both cannulae while keeping the working cannula within the visual field of the irrigation cannula).

Reference is now made to FIGS. 8A-8E which are an oblique view and a cross-section view, simplified illustrations of employment of a gripping patch in accordance with some embodiments of the invention. In some embodiments, the system and/or the device comprise a gripping patch 804 comprising at least one adhesive surface 806 configured to detachably adhere patch 804 to a surface of a cannula 618 (FIG. 8A) and/or a surface of a working/irrigation channel, e.g., a surface of working/irrigation channel furrow 604 (FIG. 8B). In some embodiments, the other side of patch 804 comprises a high-friction coefficient surface. In some embodiments, the patch 804 is resilient and configured to cushion contact between the cannula 618 and the internal surface of the working and/or irrigation channel (e.g., a surface of working/irrigation channel furrow 604.

Figure 8C:
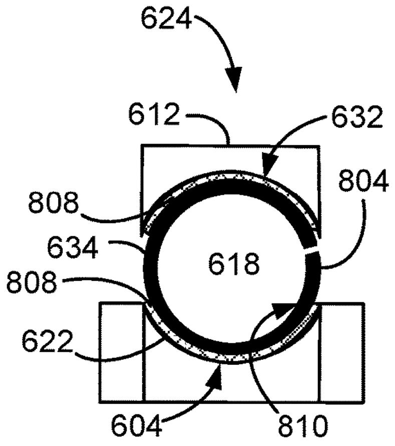

In some embodiments and as shown in FIG. 8C, a surface 622 of furrow 604 and/or an inner surface 632 of furrow cover 612 comprise an integral high-friction-coefficient surface 808 (e.g., grooved, roughened, ridged or similar) and patch 804 comprising an outer high-friction-coefficient surface 810. In some embodiments, patch 804 is resilient.

Figure 8D:
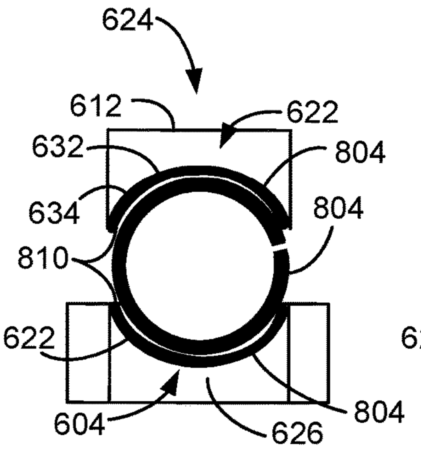

In some embodiments and as shown in FIG. 8D, a surface 622 of furrow 604 and/or an inner surface 632 of furrow cover 612 comprise a high-friction-coefficient layer 624 as explained elsewhere herein. Alternatively, in some embodiments, a patch 804 comprising an outer high-friction-coefficient surface 810 is adhered to surface 622 of furrow 604 and/or an inner surface 632 of furrow cover 612.

Figure 8E:
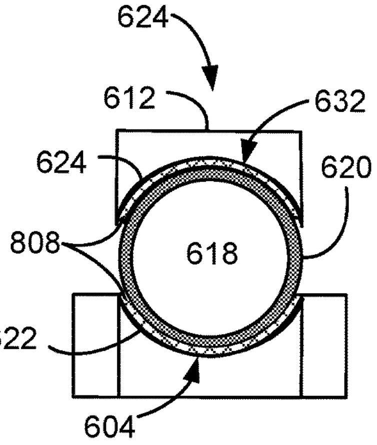

In the exemplary embodiment shown in FIG. 8E, a surface 622 of furrow 604 and/or an inner surface 632 of furrow cover 612 comprise an integral high-friction-coefficient surface 808 (e.g., grooved, uneven, ridged or similar) and a resilient sleeve 620 (e.g., rubber, Silicone or Polyurethane of low shore grades) is fitted over at least a portion of a cannula 618. A potential advantage of this configuration is in that it provides cushioning to cannula 618 as well as protection from clamping forces applied by furrow 604 and furrow cover 612 when locking nut 610 is tightened while maintaining retentiveness.

Figure 9A:
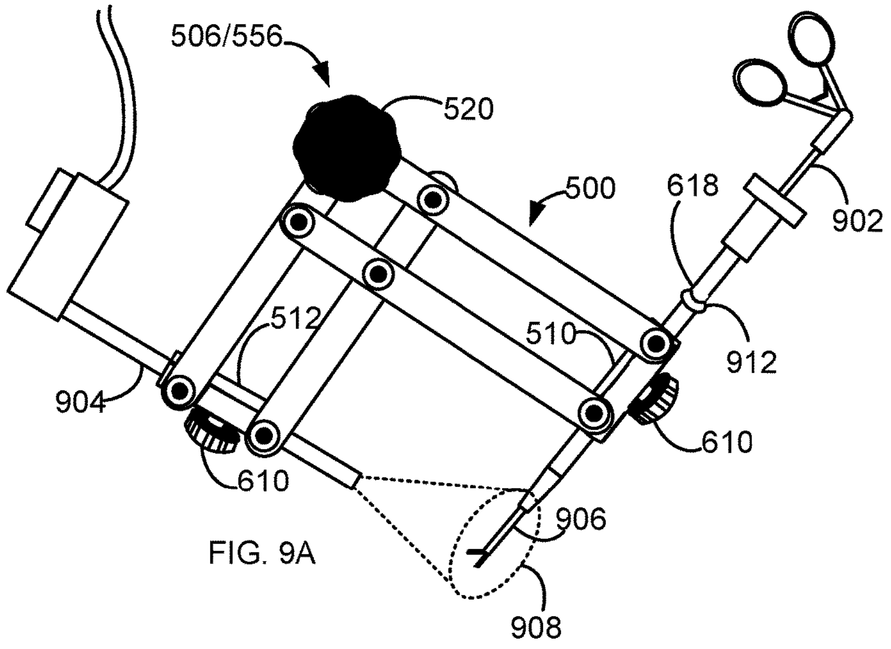
FIGS. 9A and 9B are side view simplified illustrations of implementation of an arthroscopy guide device in accordance with some embodiments of the invention.
Figure 9B:
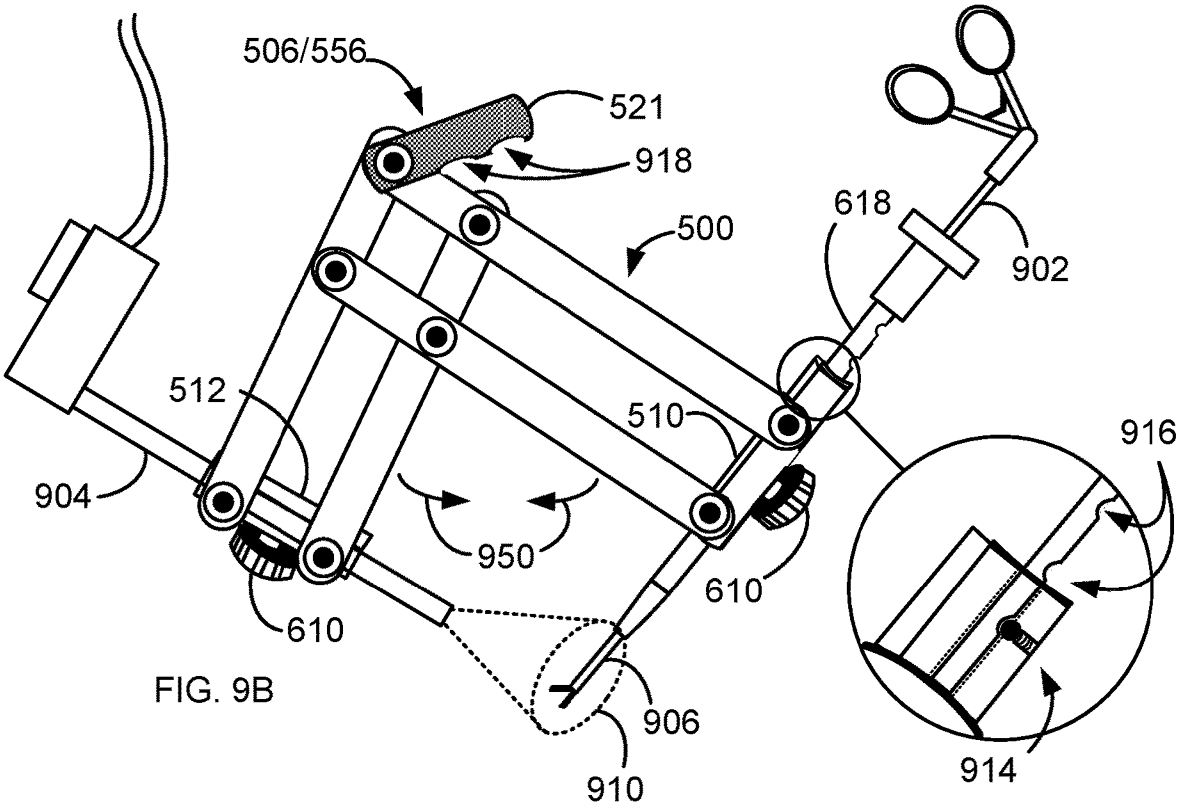

Referring now to FIGS. 9A and 9B, which are side view simplified illustrations of implementation of an arthroscopy guide device in accordance with some embodiments of the invention. The tools depicted in FIGS. 9A and 9B are brought forth for illustrative purposes and are not necessarily drawn to proportion. As shown in the exemplary embodiment depicted in FIGS. 9A and 9B, guide device 500 accommodates in a first channel holder (e.g., channel holder 510) a cannula 618 accommodating a working tool 902 (e.g., arthroscopic forceps). A second channel holder (e.g., channel holder 512) accommodates a viewing tool (e.g., a video TMJ arthroscope endoscope) 904. As shown in the exemplary embodiment depicted in FIG. 9A, the distal end 906 of working tool 902 is viewed within an FOV 908 of viewing tool 904. Adjustment of guide device 500 as indicated by arrows 950 shown in FIG. 9B, results in a reduced FOV 910 of viewing tool 904 but maintains the distal end 906 of working tool 902 within the FOV 910 of viewing tool 904.

Additionally, and optionally and as shown in FIG. 9A, in some embodiments, one or more cannulas and/or channel holders 510/512 comprises a cannula insertion limiter 912/914. In some embodiments, cannula insertion limiter 912 limits over-insertion of the cannula to prevent distal end 906 of a working tool from being positioned outside a viewing tool 904 FOV 910. Additionally, and optionally and as shown in FIG. 9B, in some embodiments, cannula insertion limiter 914 comprises a spring-loaded ball and notch system 914 configured to fit in notches made in a wall of a working cannula at predetermined distances.

A potential advantage of a cannula insertion limiter is in that it is configured to enable controlled axial adjustment of a cannula inside one or more holding channels 510/512. For example, in cases in which adjustment of device 500 is required beyond a minimal angle ($\alpha_{min}$) or a maximal angle ($\alpha_{max}$) as explained elsewhere herein, at which view of the distal end of the working tool may not be optimized and may require, for example, axial movement of working tool 902 and/or viewing tool 904. A potential advantage of a cannula insertion limiter is in that it allows stepped advancement of a cannula in cannula holder and provides an auditory indication (e.g., a clicking sound) for a user as to the advancement of the cannula inside the holder.

Figure 10A:
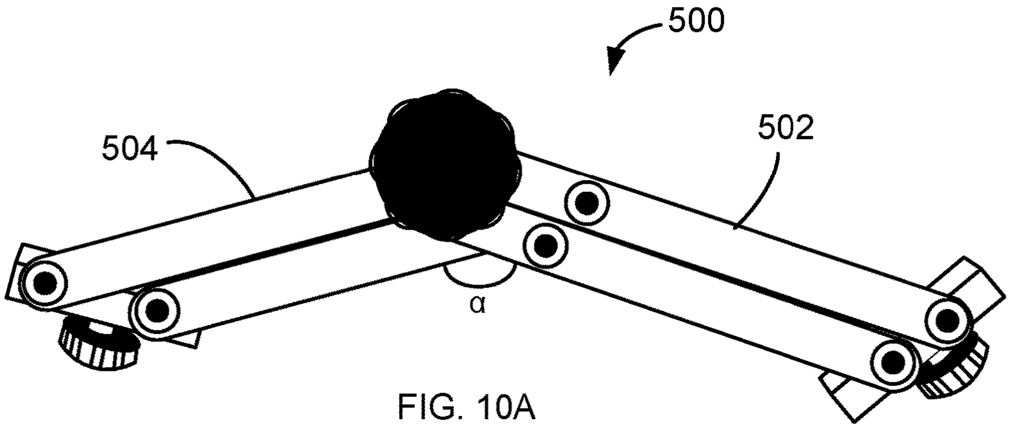
FIGS. 10A and 10B are side view simplified illustrations of an arthroscopy guide device in accordance with some embodiments of the invention.
Figure 10B:
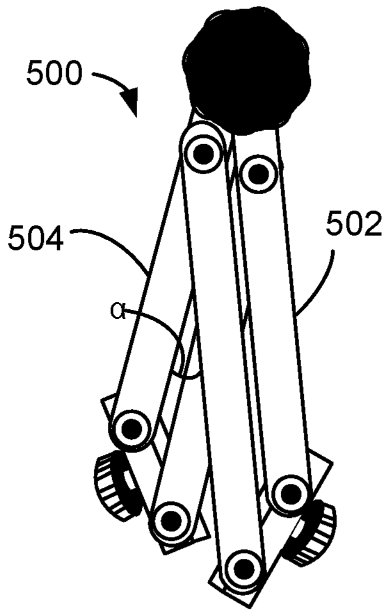

Reference is now made to FIGS. 10A and 10B, which are side view simplified illustrations of an arthroscopy guide device in accordance with some embodiments of the invention. As illustrated in the exemplary embodiment depicted in FIGS. 10A and 10B, guide device 500 is adjustable from a fully extended state (FIG. 10A) to a fully retracted state (FIG. 10B). The maximal extension as well as the minimal retraction of guide device 500 depends mainly on the length of arms 502/504 and location of revolute joints 506 along arms 502/504. In some embodiments, an angle ($\alpha$) between adjacent pivotly connected arms 502 and 504 is between 180 degrees in a fully extended state and 0 (zero) degrees in a fully retracted state. In some embodiments, an angle ($\alpha$) between adjacent pivotly connected arms 502 and 504 is between 150 degrees in a fully extended state and 30 degrees in a fully retracted state. In some embodiments, an angle ($\alpha$) between adjacent pivotly connected arms 502 and 504 is between 135 degrees in a fully extended state to 45 degrees in a fully retracted state.

Figure 11:
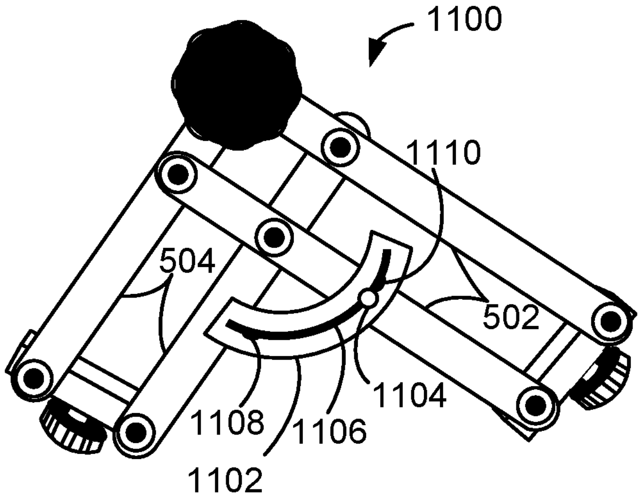
FIG. 11 is a side view simplified illustration of an arthroscopy guide device in accordance with some embodiments of the invention.

Though the range of extension/retraction is wide, beyond a certain degree of extension or retraction the view of the distal end of the working tool may not be optimized due to formation of extreme intersecting angles at intersection 44, which can be expressed by loss of view of distal end 906 of working tool 902. In some embodiments, an as shown in FIG. 11, which is a side view simplified illustration of an arthroscopy guide device in accordance with some embodiments of the invention, guide device 1100 comprises a slotted protractor 1002 coupled at one end to at least one of arms 502/504 (e.g., arm 504-1) and slidable over an adjacent pivotly connected arm 504/502 (e.g., arm 502-2), which includes a pin 1104 fixed to a surface of the arm and protrudes through a slot 1106 in protractor 1102. In some embodiments, pin 1104 is biased radially outwards in respect to protractor 1102 slot 1106. In some embodiments, slot 1106 comprises one or more notches 1108/1110 along slot 1106 that define respectively a minimal angle ($\alpha_{min}$) and a maximal angle ($\alpha_{max}$) beyond which view of the distal end of the working tool may not be optimized and may require, for example, axial movement of working tool 902 and/or viewing tool 904.

In some instances, an adjustment of guide device needs to be made mid-procedure while a surgeon needs to maintain sight of the distal end 906 of working tool 902. In such an instance, the surgeon adjusts the guide device by adjusting angle ($\alpha$). During the adjustment, pin 1104 slides along slot 1106. When extending guide device 500 and upon approaching angle ($\alpha_{max}$), pin 1104, biased radially outwards, clicks into notch 1110 making a clicking sound and signaling the surgeon he/she is approaching angle ($\alpha_{max}$). When retracting guide device 500 and upon approaching angle ($\alpha_{min}$), pin 1104, biased radially outwards, clicks into notch 1108 making a clicking sound and signaling the surgeon he/she is approaching angle ($\alpha_{min}$).

A potential advantage in this embodiment is in that guide device 500 is configured to be adjusted mid-procedure while maintaining a line of sight between viewing device 904 and distal end of working device 906.

Figure 12:
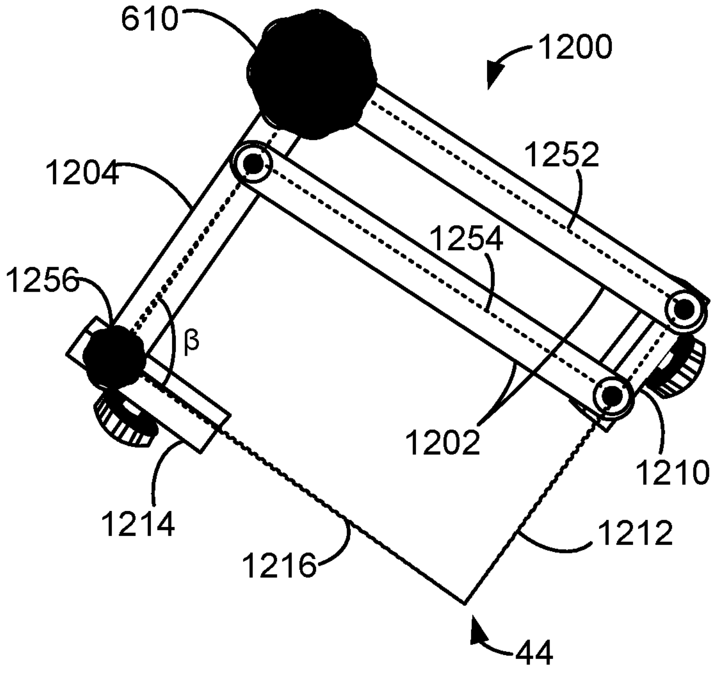
FIG. 12 is a side view simplified illustration of an arthroscopy guide device in accordance with some embodiments of the invention.

Reference is now made to FIG. 12, which is a side view simplified illustration of an arthroscopy guide device in accordance with some embodiments of the invention. In the exemplary embodiment depicted in FIG. 12, a guide device 1200 comprises one or more pairs of arms 1202 pivotly connected at one end to at least one arm 1204 to form with arm 1204 one or more adjustable parallelograms 1252/1254. In some embodiments, guide device 1200 comprises a locking nut 610 positioned as explained elsewhere herein.

As explained elsewhere herein, one or more pairs of arms 1202 and at least one arm 1204 are connected to a channel holder. In some embodiments and as explained elsewhere herein, the channel holder comprises at least one of a working cannula holder 1210 and an irrigation/viewing cannula holder 1214. In some embodiments, for example, one or more pairs of arms 1202 are connected to a working cannula holder 1210 defining a working cannula axis 1212, and arm 1204 is connected to an irrigation/viewing cannula holder 1214 defining an irrigation cannula axis 1216. In some embodiments, and as shown in FIG. 12, irrigation cannula axis 1216 intersects with working cannula axis 1212 at an intersection 44. In some embodiments, intersection 44 and locking nut 610 are located at opposing vertices of at least one of adjustable parallelograms 1252/1254.

In some embodiments, one or more channel holders (e.g., an irrigation/viewing cannula holder 1214) is connected to arm 1204. In some embodiments, irrigation/viewing cannula holder 1214 is rigidly coupled to arm 1204 at a predetermined angle ($\beta$) between longitudinal axes of irrigation/viewing cannula holder 1214 and arm 1204. Alternatively, and optionally, guide device 1200 comprises a second locking joint 1256, adjustable from an open-unlocked position that allows adjustment of irrigation/viewing cannula holder 1214 to a closed-locked position that fixes the orientation (e.g., angle ($\beta$) of irrigation/viewing cannula holder 1214 in respect to arm 1204.

In some embodiments, the device is devoid of a working channel. In some such embodiments, the working channel holder of the device is configured to hold a specific type or size of cannula for use as a working channel. In other such embodiments, the working channel holder of the device is configured to be adaptable to hold various types and/or sizes of cannula for use as a working channel.

In some embodiments, the device is devoid of an irrigation channel. In some such embodiments, the irrigation channel holder of the device is configured to hold a specific type or size of cannula for use as an irrigation channel. In other such embodiments, the irrigation channel holder of the device is configured to be adaptable to hold various types and/or sizes of cannula for use as an irrigation channel. In some such embodiments, the device is also device of an observation channel, as described in the preceding paragraph.

In some embodiments, the device comprises an irrigation channel as a component. In some such embodiments, the irrigation channel is reversibly attached to the irrigation channel holder. In some such embodiments, the irrigation channel is fixedly attached to the irrigation channel holder. As noted above, in some embodiments, the device is configured to allow axial rotation of an irrigation channel attached to the irrigation channel holder, but in other embodiments, no such rotation is possible. In some embodiments, the device is configured to allow axial sliding of an irrigation channel attached to the irrigation channel holder, but in other embodiments no such sliding is possible.

In some embodiments, the device comprises a working channel as a component. In some such embodiments, the working channel is reversibly attached to the working channel holder. In some such embodiments, the working channel is fixedly attached to the working channel holder. As noted above, in some embodiments, the device is configured to allow axial rotation of a working channel attached to the working channel holder, but in other embodiments, no such rotation is possible. In some embodiments, the device is configured to allow axial sliding of a working channel attached to the working channel holder, but in other embodiments no such sliding is possible.

In some embodiments, a guide device as described herein is provided together with a working channel, an irrigation channel or both a working channel and an irrigation channel as a kit.

Thus, according to an aspect of some embodiments of the teachings herein, there is also provided a kit comprising: a guide device according to the teachings herein; and a working channel configured for physical association with the working channel holder of the guide device. In some such embodiments, the kit further comprises an irrigation channel, configured for physical association with the irrigation channel holder of the guide device.

Thus, according to an aspect of some embodiments of the teachings herein, there is also provided a kit comprising: a guide device according to the teachings herein; and an irrigation channel configured for physical association with the irrigation channel holder of the guide device. In some such embodiments, the kit further comprises a working channel, configured for physical association with the working channel holder of the guide device.

Embodiments of the invention have been described herein primarily with reference to treatment of living human subjects. It is understood, however, that embodiments of the invention are performed for the veterinary or industrial (agriculture) treatment of a non-human mammal, such as pigs and other porcine, dogs and other canids, cats and other felines, horses and other equines, monkeys, apes and bovines.

Embodiments of the invention have been described herein primarily with reference to treatment of living subjects. It is understood that application of the invention for training and educational purposes (as opposed to treating a condition) falls within the scope of the claims, whether on a living non-human subject or on a dead subject, whether on a simulated human body, a human cadaver or on a non-human body, whether on a eye isolated (at least partially) from a body, or on a body.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

Citation or identification of any reference in this application shall not be construed as an admission that such reference is available as prior art to the invention.

Section headings are used herein to ease understanding of the specification and should not be construed as necessarily limiting.

What is claimed is:

1. A guide device useful for assisting in performance of TMJ arthroscopy, comprising:

a working channel holder defining a working channel axis and an irrigation channel holder defining an irrigation channel axis, said working channel axis and said irrigation channel axis substantially intersecting at an intersection that is within a specific empty volume, at an intersection angle;

a plurality of linkages mutually connected by a plurality of parallel-axis revolute joints, said revolute joints defining the vertices of a plurality of parallelograms having sides with fixed lengths with angles changeable by rotation of said linkages around said revolute joints;

wherein a first of said plurality of parallelograms comprises as vertices two of said revolute joints that are connected to said working channel holder;

wherein a second of said plurality of parallelograms comprises as vertices two of said revolute joints that are connected to said irrigation channel holder; and wherein a third of said plurality of parallelograms comprises said intersection as a vertex; and wherein said parallelograms are physically linked so that the distance of said intersection from said working channel holder and from said irrigation channel holder remains constant while said intersection angle changes during said rotation of said linkages around said revolute joints.

2. The device of claim 1, wherein said plurality of linkages comprises at least six rigid linkages mutually connected by said plurality of parallel-axis revolute joints comprising at least seven parallel-axis revolute joints.

3. The device of claim 1, wherein a length of a proximal transmission link and a length of a distal proximal length are adjustable.

4. The device of claim 1, further comprising a rotation lock, allowing reversible fixing of an angle of rotation of said revolute joints.

5. The device of claim 1, comprising a channel lock configured to reversibly secure a cannula held in said channel holder.

6. The device of claim 1, wherein said working channel holder directly rigidly connects a third and a sixth of said revolute joints.

7. The device of claim 1, wherein said working channel holder comprises two physically separate working channel holder parts, a first said part connected to said third revolute joint and a second said part connected to said sixth said revolute joint.

8. The device of claim 1, wherein said irrigation channel holder directly rigidly connects a seventh and an eighth of said revolute joints.

9. The device of claim 1, wherein said irrigation channel holder comprises two physically separate irrigation channel holder parts, a first said part connected to said seventh revolute joint and a second said irrigation channel holder part connected to said eighth said revolute joint.

10. The device of claim 1, said irrigation channel holder configured to allow reversible attachment of an irrigation channel to said irrigation channel holder.

11. The guide device according to claim 1, wherein said working channel holder comprises a body having a furrow and a cover, at least a surface of said furrow and an inner surface of said cover comprise at least one layer of a resilient and/or retentive material.

12. The guide device according to claim 11, wherein said material comprises at least one layer of a high-friction coefficient material and at last one layer of resilient material between said high-friction coefficient material and at least one of said surfaces.

13. The guide device according to claim 11, wherein said body holder is configured to concurrently allow movement of a tip of a tool held between said furrow and said cover and retain said tool within said holder.

* * * * *